United States Patent
Hodshon et al.

(10) Patent No.: US 9,918,836 B2
(45) Date of Patent: *Mar. 20, 2018

(54) PROSTHETIC HEART VALVE PACKAGING AND DEPLOYMENT METHODS

(71) Applicant: Edwards Lifesciences Corporation, Irvine, CA (US)

(72) Inventors: Fred Hodshon, Orange, CA (US); Rafael Pintor, Mission Viejo, CA (US); August R. Yambao, Temecula, CA (US); Abishek Gautam, Irvine, CA (US); Louis A. Campbell, Santa Ana, CA (US); Lawrence J. Farhat, Carlsbad, CA (US); Tammy Huntley, Santa Ana, CA (US); Faisal Kalam, Corona, CA (US); Travis Zenyo Oba, Yorba Linda, CA (US); Qinggang Zeng, Aliso Veijo, CA (US)

(73) Assignee: Edwards Lifesciences Corporation, Irvine, CA (US)

(*) Notice: Subject to any disclaimer, the term of this patent is extended or adjusted under 35 U.S.C. 154(b) by 25 days.

This patent is subject to a terminal disclaimer.

(21) Appl. No.: 15/068,324

(22) Filed: Mar. 11, 2016

(65) Prior Publication Data
US 2016/0262882 A1    Sep. 15, 2016

Related U.S. Application Data

(60) Continuation of application No. 13/403,537, filed on Feb. 23, 2012, now Pat. No. 9,295,539, which is a
(Continued)

(51) Int. Cl.
   A61F 2/24        (2006.01)
   A61F 2/00        (2006.01)

(52) U.S. Cl.
   CPC .......... *A61F 2/2427* (2013.01); *A61F 2/0095* (2013.01); *A61F 2/24* (2013.01);
   (Continued)

(58) Field of Classification Search
   CPC ........ A61F 2/0095; A61F 2/24; A61F 2/2409; A61F 2/2427; A61F 2/2418
   (Continued)

(56) References Cited

U.S. PATENT DOCUMENTS 4,101,031 A    7/1978   Cromie
4,182,446 A    1/1980   Penny
(Continued)

*Primary Examiner* — Vy Bui
(74) *Attorney, Agent, or Firm* — Guy Cumberbatch, Esq.

(57) ABSTRACT

Packaging for prosthetic heart valves including an assembly for securely retaining a heart valve within a jar and facilitating retrieval therefrom. The assembly includes a packaging sleeve that fits closely within the jar and has a clip structure for securing a valve holder. Contrary to previous designs, in one embodiment the valve holder is directed downward into the jar, and the valve is retained with an inflow end upward. The valve may have flexible leaflets, and a leaflet parting member on the end of the shaft extends through the leaflets and couples with the valve holder. The assembly of the packaging sleeve, valve, and holder can then be removed from the jar and a valve delivery tube connected with the holder, or to the leaflet parting member. The packaging sleeve may be bifurcated into two halves connected at a living hinge to facilitate removal from around the valve/holder subassembly.

24 Claims, 12 Drawing Sheets

Related U.S. Application Data division of application No. 12/969,238, filed on Dec. 15, 2010, now Pat. No. 8,869,982.

(60) Provisional application No. 61/287,807, filed on Dec. 18, 2009, provisional application No. 61/287,806, filed on Dec. 18, 2009.

(52) U.S. Cl.
CPC .......... *A61F 2/2409* (2013.01); *A61F 2/2412* (2013.01); *A61F 2/2418* (2013.01); *A61F 2220/0075* (2013.01)

(58) Field of Classification Search
USPC ......... 623/2.11, 2.12, 2.17, 2.18, 2.24, 2.26; 206/205, 210, 438; 606/1
See application file for complete search history.

(56) References Cited

U.S. PATENT DOCUMENTS

| | | | |
|---|---|---|---|
| 4,211,325 A | 7/1980 | Wright | |
| 4,697,703 A | 10/1987 | Will | |
| 4,801,015 A | 1/1989 | Lubock et al. | |
| 5,167,223 A | 12/1992 | Koros et al. | |
| 5,197,979 A * | 3/1993 | Quintero | A61F 2/2427 623/1.26 |
| 5,236,450 A | 8/1993 | Scott | |
| 5,480,425 A | 1/1996 | Ogilive | |
| 5,531,785 A | 7/1996 | Love et al. | |
| 5,560,487 A | 10/1996 | Starr | |
| 5,578,076 A | 11/1996 | Krueger et al. | |
| 5,582,607 A | 12/1996 | Lackman | |
| 5,615,770 A | 4/1997 | Applebaum et al. | |
| 5,690,226 A | 11/1997 | N'Guyen | |
| 5,720,391 A | 2/1998 | Dohm et al. | |
| 5,776,187 A | 7/1998 | Krueger et al. | |
| 5,800,531 A | 9/1998 | Cosgrove et al. | |
| 5,823,342 A | 10/1998 | Caudillo et al. | |
| 5,868,253 A | 2/1999 | Krueger et al. | |
| 5,980,569 A | 11/1999 | Scirica | |
| 5,984,959 A | 11/1999 | Robertson et al. | |
| 6,090,138 A | 7/2000 | Chasak et al. | |
| 6,126,007 A | 10/2000 | Kari et al. | |
| 6,197,053 B1 | 3/2001 | Cosgrove et al. | |
| 6,199,696 B1 | 3/2001 | Lytle et al. | |
| 6,346,094 B2 | 2/2002 | West et al. | |
| 6,409,758 B2 | 6/2002 | Stobie et al. | |
| 6,416,547 B1 | 7/2002 | Erickson et al. | |
| 6,534,004 B2 | 3/2003 | Chen et al. | |
| 6,591,998 B2 | 7/2003 | Haynes et al. | |
| 6,702,852 B2 | 3/2004 | Stobie et al. | |
| 6,723,122 B2 | 4/2004 | Yang et al. | |
| 6,736,845 B2 | 5/2004 | Marquez et al. | |
| 6,966,925 B2 * | 11/2005 | Stobie | A61F 2/2427 623/2.11 |
| 7,389,874 B2 | 6/2008 | Quest et al. | |
| 7,699,168 B2 | 4/2010 | Ryan et al. | |
| 7,712,606 B2 | 5/2010 | Salahieh et al. | |
| 2002/0120328 A1 | 8/2002 | Pathak et al. | |
| 2006/0015177 A1 | 1/2006 | Quest et al. | |
| 2006/0019183 A1 | 1/2006 | Voisin | |
| 2006/0113207 A1 | 6/2006 | Ryan et al. | |
| 2009/0130162 A2 | 5/2009 | Pathak et al. | |
| 2009/0164005 A1 | 6/2009 | Dove et al. | |
| 2011/0147251 A1 | 6/2011 | Hodshon et al. | |

\* cited by examiner

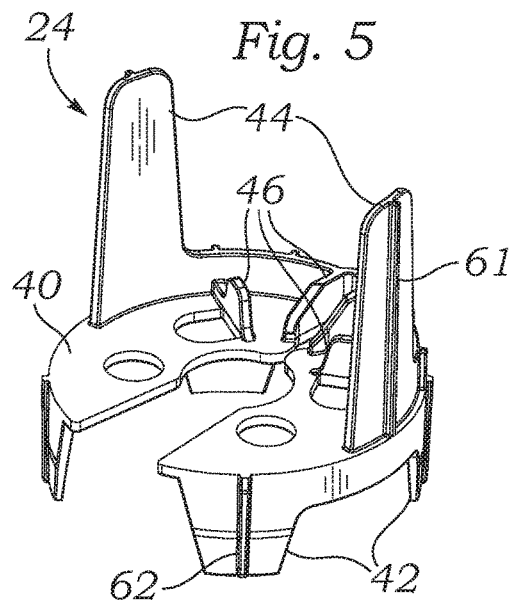
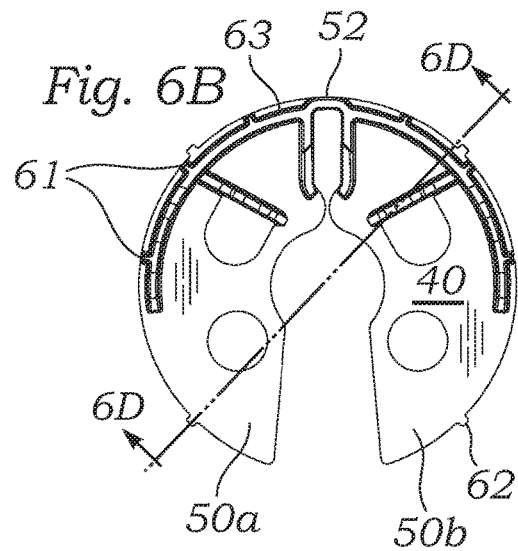
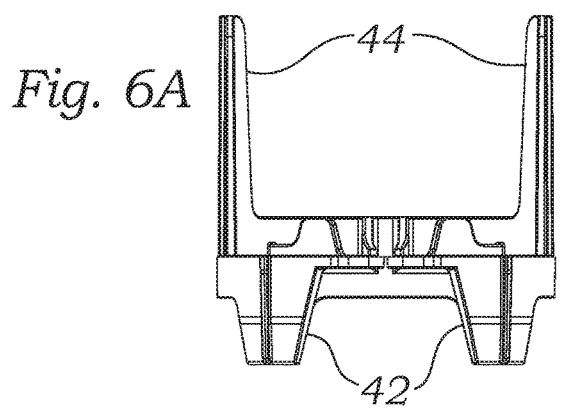
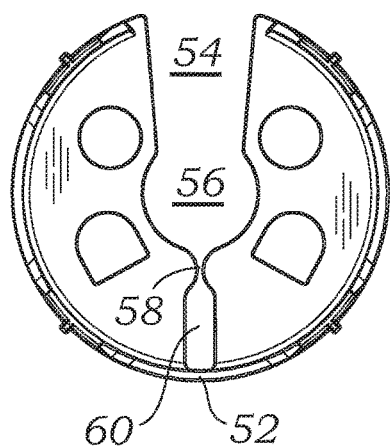

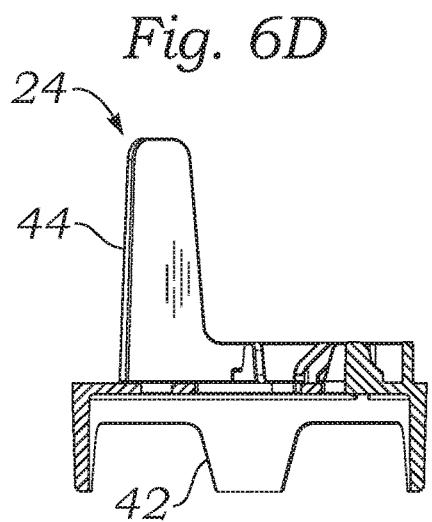
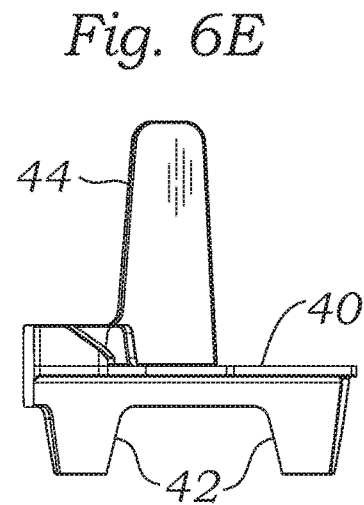
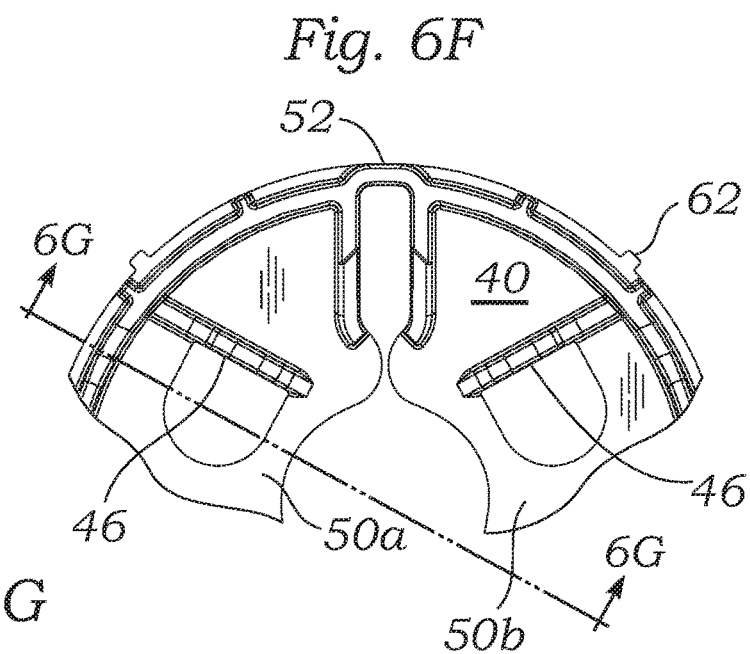
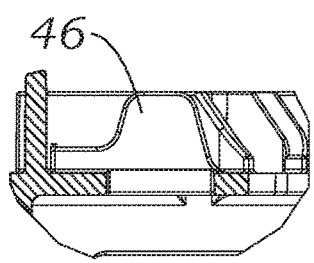

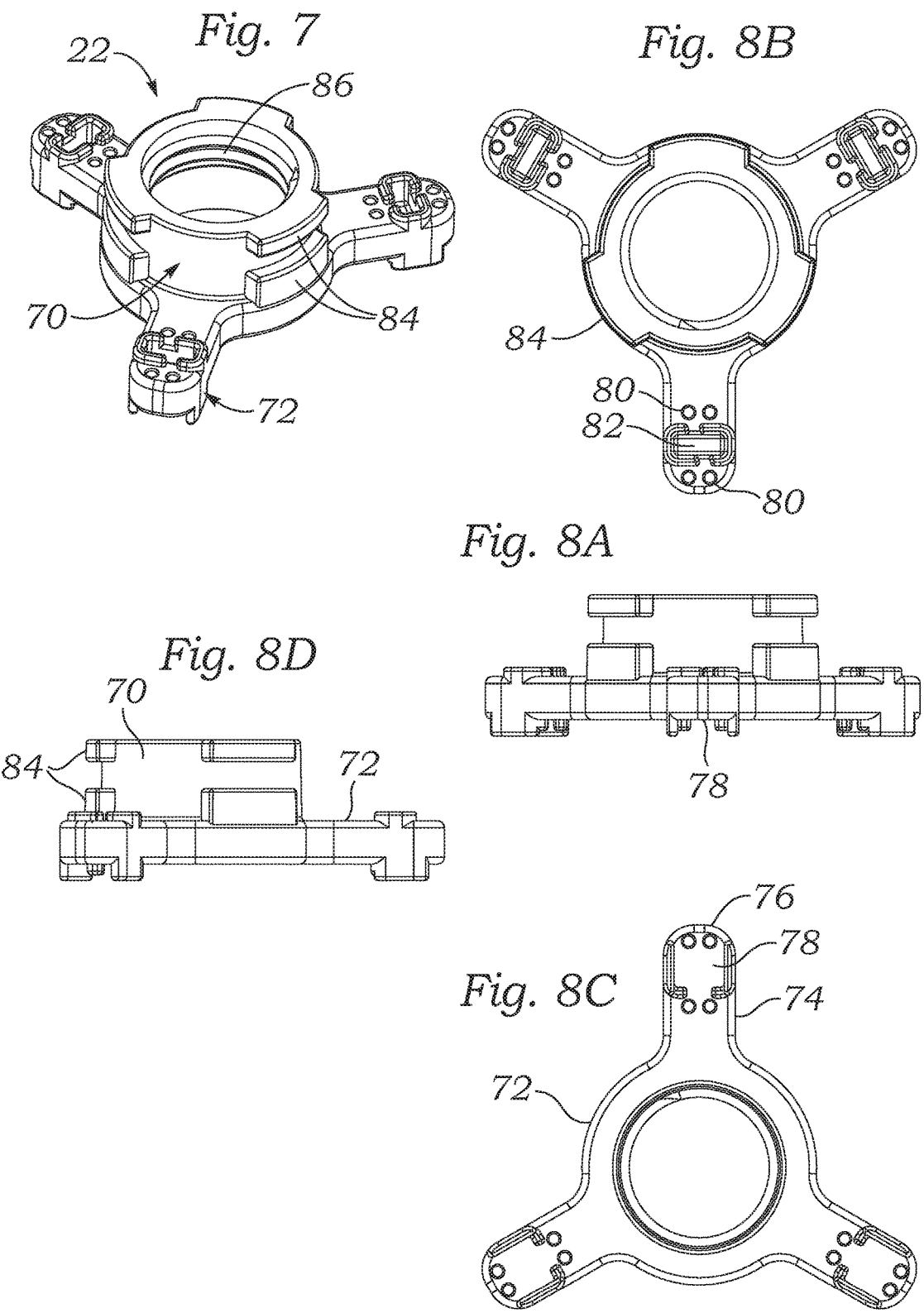

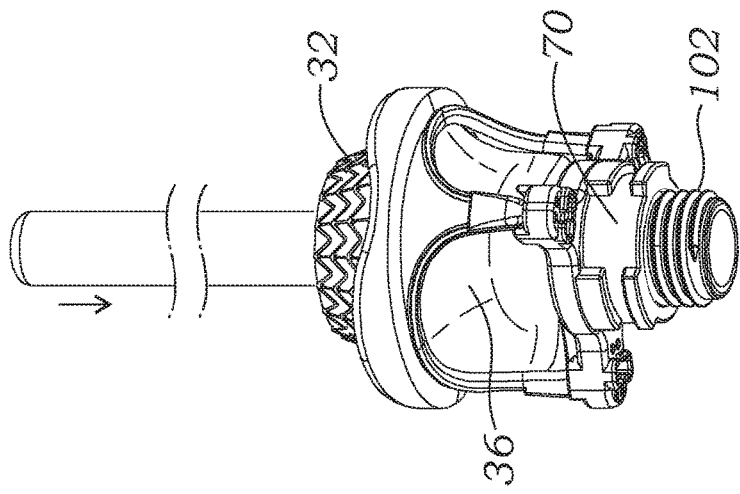
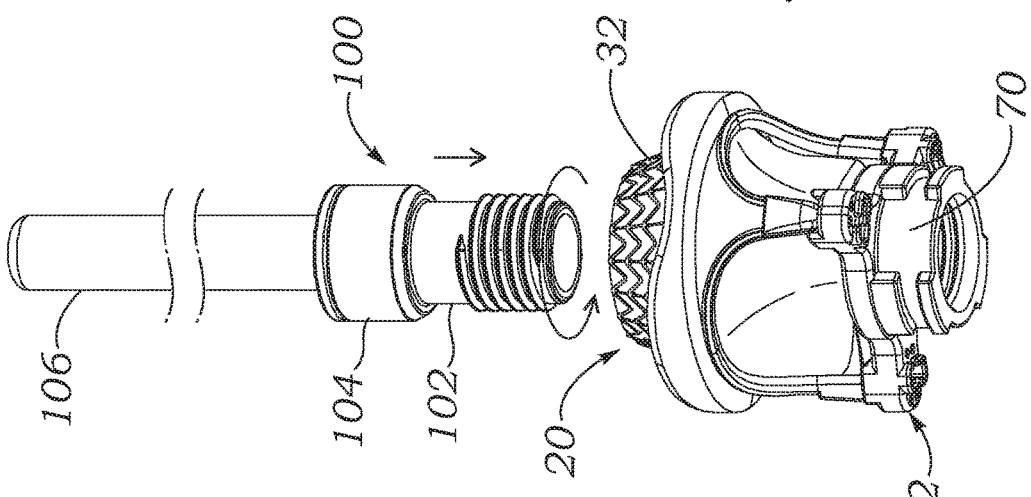
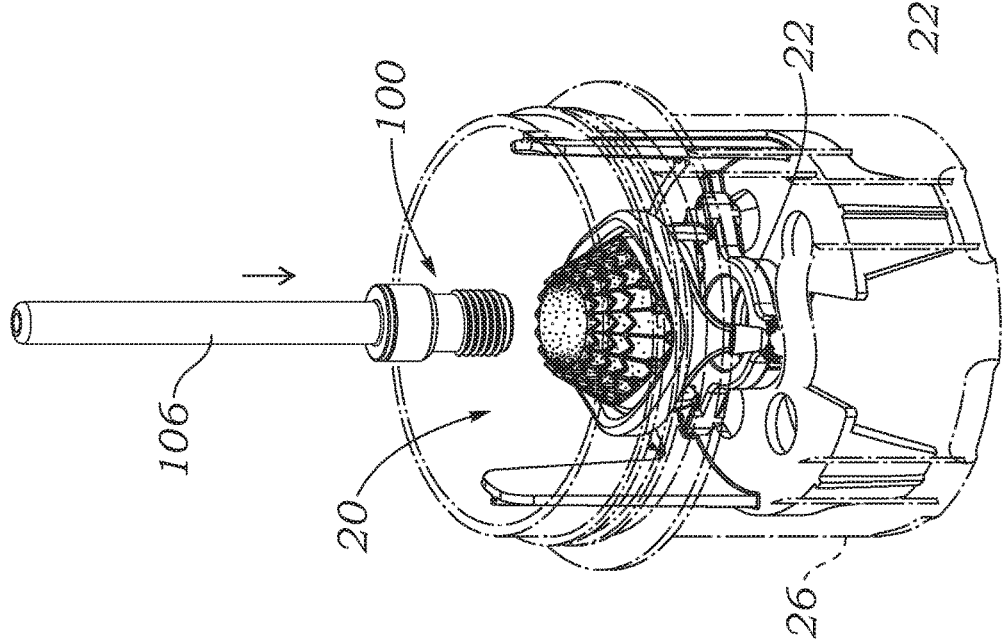

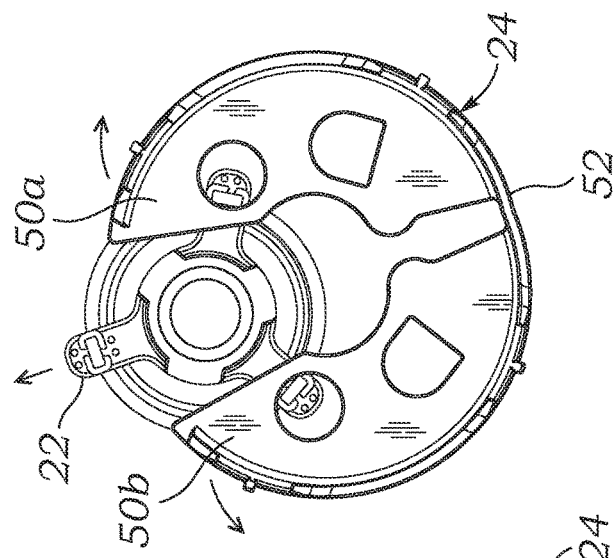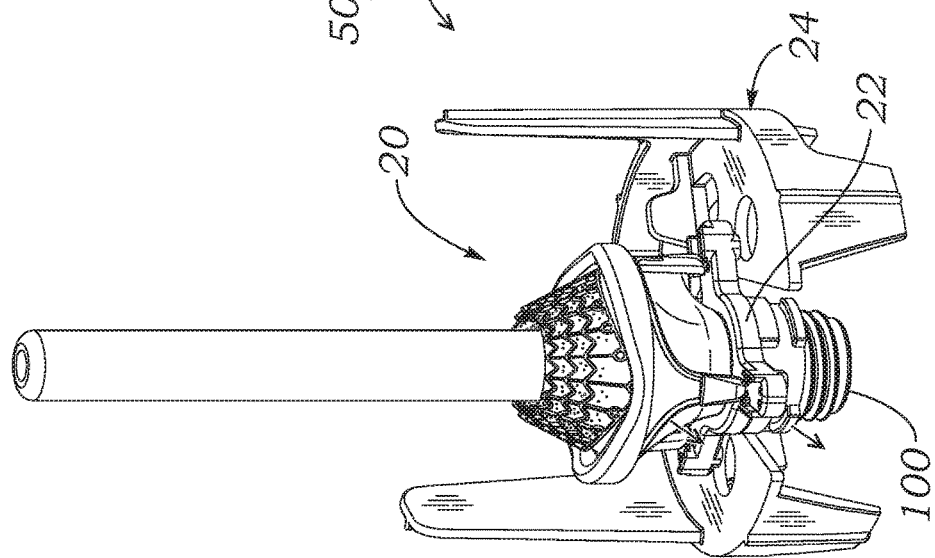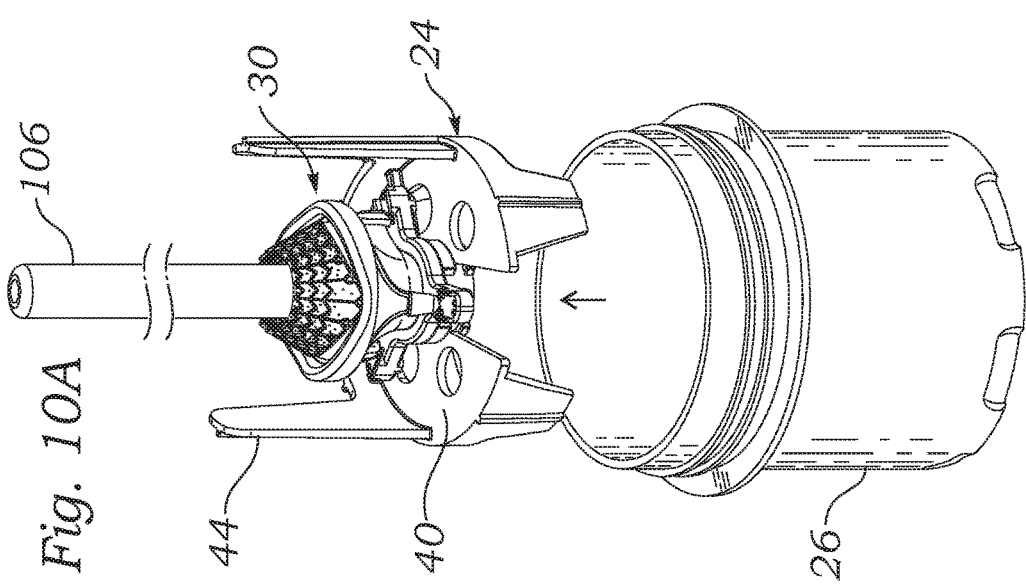

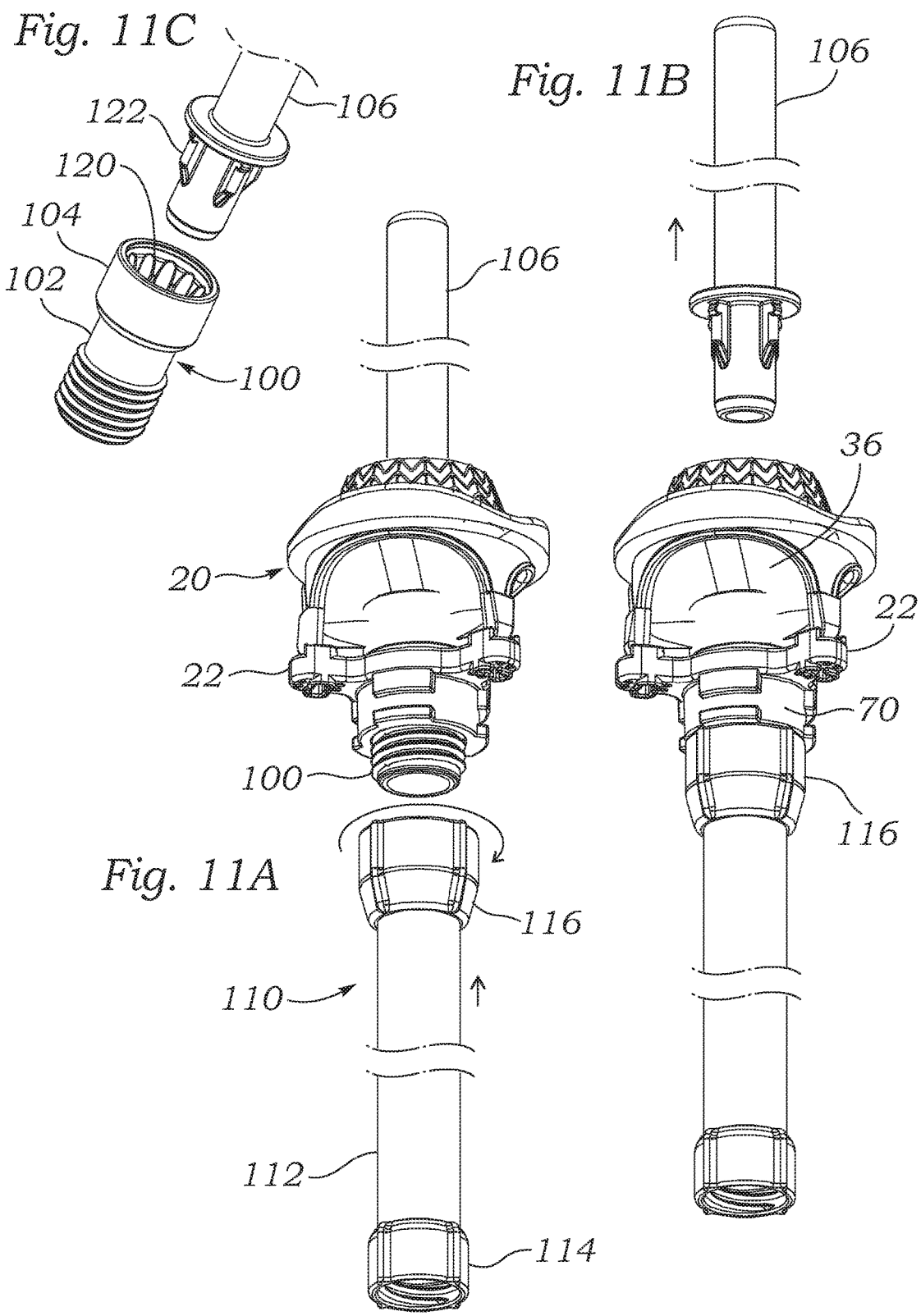

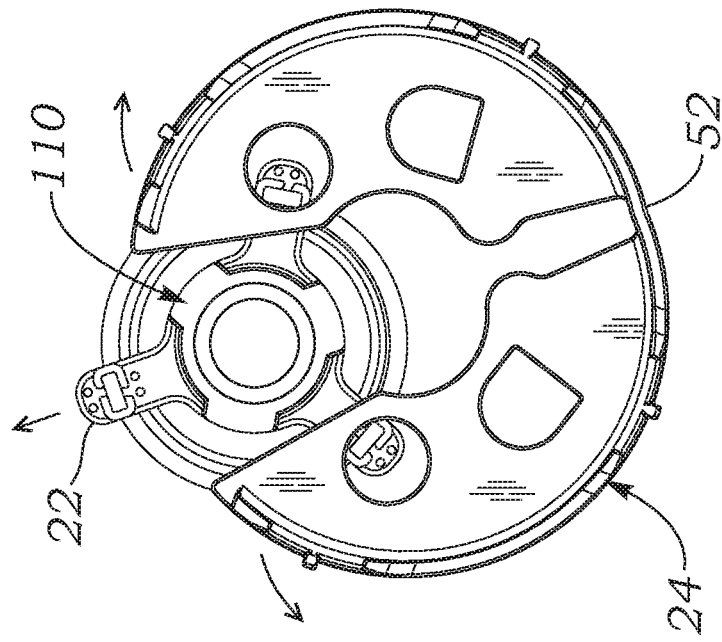
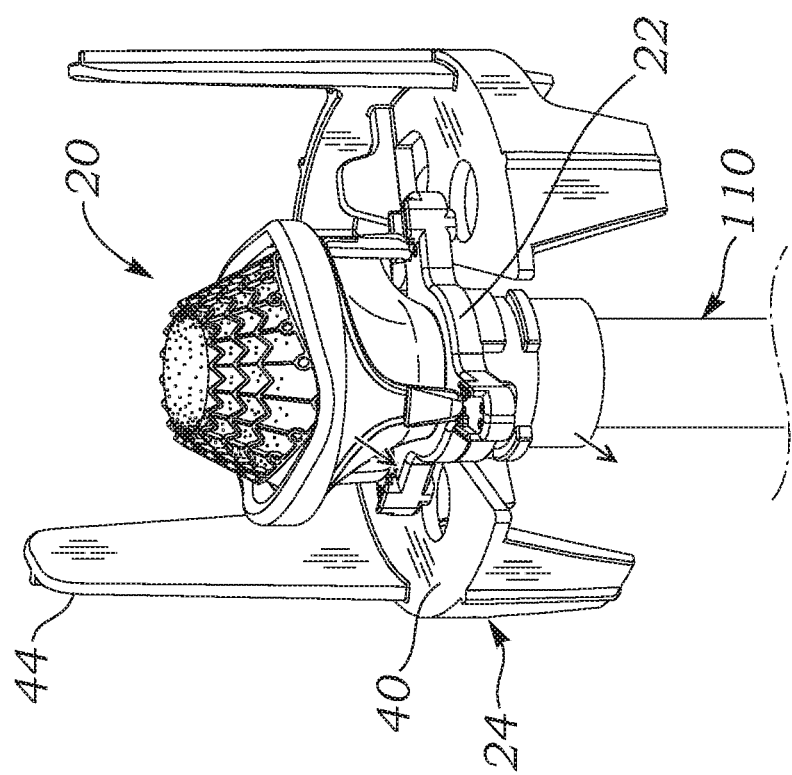

PROSTHETIC HEART VALVE PACKAGING AND DEPLOYMENT METHODS

RELATED APPLICATIONS

This application is a continuation of U.S. application Ser. No. 13/403,537, filed Feb. 23, 2012, which is a divisional of U.S. application Ser. No. 12/969,238, filed Dec. 15, 2010, now U.S. Pat. No. 8,869,982, which claims the benefit of U.S. Application No. 61/287,806, filed Dec. 18, 2009, and U.S. Application No. 61/287,807, filed Dec. 18, 2009, the entire disclosures of which are incorporated by reference herein.

FIELD OF THE INVENTION

The present invention generally relates to packaging for prosthetic heart valves and, more particularly, to an assembly and methods for securely retaining a heart valve within a fluid-filled jar and facilitating retrieval therefrom.

BACKGROUND OF THE INVENTION

Heart valve disease continues to be a significant cause of morbidity and mortality, resulting from a number of ailments including rheumatic fever and birth defects. Currently, the primary treatment of aortic valve disease is valve replacement. Worldwide, approximately 300,000 heart valve replacement surgeries are performed annually, and about one-half of these patients received mechanical heart valves, which are composed of rigid, synthetic materials. The remaining patients received bioprosthetic heart valve replacements, which utilize biologically derived tissues for flexible fluid occluding leaflets.

The most successful bioprosthetic materials for flexible leaflets are whole porcine valves and separate leaflets made from bovine pericardium stitched together to form a tri-leaflet valve. However, flexible leaflets formed of polymeric, fiber-reinforced, and other synthetic materials have also been proposed. The most common flexible leaflet valve construction includes three leaflets mounted to commissure posts around a peripheral non-expandable support structure with free edges that project toward an outflow direction and meet or coapt in the middle of the flowstream. A suture-permeable sewing ring is provided around the inflow end.

Bioprosthetic heart valves are packaged in jars filled with preserving solution for shipping and storage prior to use in the operating theater. To minimize the possibility of damage to the relatively delicate bioprosthetic heart valves, they are stabilized with bracketing structure to prevent them from striking the inside of the jar. Prior to implantation in a patient, the valve is removed from the jar and then rinsed in a shower or immersed and agitated in a bath.

The majority of prosthetic valves are destined for either the mitral or aortic position, though to a much lesser extent tricuspid and pulmonary replacements are made. The conventional surgical delivery path for mitral and aortic replacements is from above; down the right atrium for mitral valves and down the ascending aorta for aortic valves. (Of course, these directions are relative to the upright human, and with the patient lying supine up and down become horizontal). The blood flow direction in these two positions is opposite, with blood flowing down from the right atrium through the mitral valve and into the left ventricle, and then up from the left ventricle through the aortic valve and into the ascending aorta. Therefore, the mitral valve is normally distally advanced with the inflow side up (or proximal), and the aortic valve is advanced with the outflow side up. Prosthetic valves typically have a valve holder centrally located and sutured thereto, and the holders used for both are attached to the proximal end—to the inflow sewing ring for mitral valves and to the outflow commissure tips for aortic valves—so that an attached surgical delivery handle extends proximally out of the implant site. The delivery handle usually couples to the valve holder while still in the jar and lifts the valve assembly out of the jar. Consequently, to orient the mitral valve holder facing upward in the jar the outflow leaflet commissure tips project down, while the jar orientation for aortic valves is with the inflow sewing ring extending down into the jar. Both valves are thus suspended downward from the holder into the fluid-filled jar, though inverted with respect to one another.

The valves are stabilized with various structures, including a 2- or 3-piece clip and tubular sleeve structure, such as shown in U.S. Pat. No. 6,416,547 to Erickson, et al. One function of the sleeve is to create an annular space between it and the jar for receiving a product ID tag dangling from the valve by a thread and prevent it from contacting and potentially damaging the valve leaflets. This packaging configuration is somewhat complex and time consuming to assemble and disassemble, and is somewhat limited by the aforementioned respective jar orientations for mitral and aortic valves.

In view of the foregoing, it is apparent that there is still a need in the art for alternative packaging for heart valves that enables a medical practitioner to easily and safely remove the valve, as well as attach a surgical handle thereto.

SUMMARY OF THE INVENTION

The present application provides packaging for prosthetic heart valves that securely retains the valve within a jar and facilitates retrieval therefrom. The assembly includes a packaging sleeve that fits closely within the jar and has a clip structure for securing a valve holder, preferably with an inflow end upward. The packaging system facilitates attachment of the valve delivery tube for use in a quick-connect valve implant procedure.

One aspect of the present application provides a jar packaging assembly for prosthetic heart valves, in particular aortic bioprosthetic valves having an expandable stent. An exemplary surgical procedure for which this valve is designed requires it to be packaged in an inverted position (holder towards the bottom of the jar), which is unique when compared to current suspended (holder facing up in the jar) tissue valve packaging designs. The exemplary packaging assembly includes a single piece clip/sleeve hybrid (coupler) which is intended to contain, stabilize, lock, protect and preserve the bioprosthetic valve during sterilization, transit, storage and use. Additionally, the new package is designed to facilitate attachment of a handle to allow for quick and easy valve removal and reduce overall complexity.

An exemplary aspect of the invention is a packaged prosthetic heart valve assembly with the valve inverted. The assembly includes a jar having a closed bottom, a prosthetic heart valve having an inflow end and an outflow end, and a valve holder attached to the outflow end of the valve. A packaging sleeve sized to fit closely within the jar rests on the bottom thereof. The sleeve has structure to which the valve holder removably couples such that the holder is oriented toward the bottom of the jar.

In the assembly described above, the packaging sleeve can have at least two components, one of the components being a generally planar clip and the other component circumscribing the clip and extending substantially the entire axial height of the jar between the bottom and the lid. Alternatively, the packaging sleeve comprises a single molded component having a plurality of lower legs extending downward from a generally planar clip that together elevate the clip above and generally parallel to the jar bottom. In the single component sleeve, a plurality of upstanding posts having longer lengths than the legs project upward from the clip into proximity with the jar lid, and the structure to which the valve holder removably couples is a central docking aperture of a generally planar clip that has an entry slot open to the central docking aperture. Preferably, the upstanding posts extend upward from the clip between about 60-80% of the overall axial sleeve height. The single component packaging sleeve is defined by two substantially similar halves pivotally connected together at a living hinge at the peripheral edge of the sleeve.

In one embodiment, the structure to which the valve holder removably couples is a central docking aperture of a generally planar clip from which a plurality of axial ribs extend upward and emanate generally radially from the central docking aperture. Further, the valve holder includes a central hub and legs projecting radially outward therefrom, wherein at least one of the axial ribs interferes with rotation of one of the valve holder legs when the valve holder is positioned in the central docking aperture to prevent rotation of the holder relative to the clip. The packaging sleeve may also include at least one axial anti-rotation rib projecting outward from its periphery, wherein the jar includes at least one rail projecting inward from an inner wall that interferes with movement of the anti-rotation rib to limit rotation of the sleeve within the jar.

A method of preparing a packaged prosthetic heart valve for implant disclosed herein, with the valve inverted, includes providing a packaged prosthetic heart valve having an inflow end and an outflow end. A valve holder assembles to the outflow end of the valve, and the assembly of the valve and holder is positioned within a jar with the holder oriented toward the bottom of the jar. A user extends a shaft through the middle of the heart valve from the inflow end to the outflow end, couples the shaft to the valve holder, and removes the assembly of the valve and holder from the jar using the shaft.

In the aforementioned method, a packaging sleeve sized to fit closely within the jar and rest on the bottom thereof has structure to which the valve holder removably couples, and the method includes removing the assembly of the valve, holder and packaging sleeve from the jar using the shaft. The packaging sleeve preferably comprises a single molded component having a plurality of lower legs extending downward from a generally planar clip that together elevate the clip above and generally parallel to the jar bottom, and a plurality of upstanding posts having longer lengths than the legs projecting upward from the clip into proximity with the jar lid. The structure to which the valve holder removably couples is a central docking aperture of a generally planar clip that has an entry slot open to the central docking aperture, and the method further includes decoupling the valve holder from the clip. If the packaging sleeve is a single component, it may be defined by two substantially similar halves pivotally connected together at a living hinge at the peripheral edge of the sleeve, wherein the method further includes separating the two sleeve halves to decouple the valve holder from the sleeve.

The prosthetic heart valve can include a plurality of flexible leaflets mounted to commissure posts around a peripheral non-expandable support structure with free edges that project toward an outflow direction and meet or coapt along a valve axis. The method thus may include providing a leaflet parting member on the shaft that pushes past the flexible leaflets and couples to the valve holder. Further, a valve delivery tube attaches to the leaflet parting member from the outflow side of the valve, and the shaft detaches from the leaflet parting member.

Another method of preparing a packaged prosthetic heart valve for implant, with the valve inverted, comprises providing a packaged prosthetic heart valve having flexible leaflets and an inflow end and an outflow end. A valve holder assembles to the outflow end of the valve, and the assembly of the valve and holder is positioned within a jar with the holder oriented toward the bottom of the jar. A user extends a shaft having a leaflet parting member thereon through the middle of the heart valve from the inflow end to the outflow end past the flexible leaflets and couples the leaflet parting member to the valve holder. The user removes the assembly of the valve and holder from the jar using the shaft, attaches a valve delivery tube to the leaflet parting member from the outflow side of the valve, and detaches the shaft from the leaflet parting member.

In the method described above the packaged prosthetic heart valve desirably further includes a packaging sleeve sized to fit closely within the jar and rest on the bottom thereof, the sleeve having structure to which the valve holder removably couples, and the method involves removing the assembly of the valve, holder and packaging sleeve from the jar using the shaft. The packaging sleeve may be a single molded component having a plurality of lower legs extending downward from a generally planar clip that together elevate the clip above and generally parallel to the jar bottom, and a plurality of upstanding posts having longer lengths than the legs projecting upward from the clip into proximity with the jar lid. Also, the structure to which the valve holder removably couples may be a central docking aperture of a generally planar clip that has an entry slot open to the central docking aperture, wherein the method further includes decoupling the valve holder from the clip. If the packaging sleeve is a single molded component, it may be defined by two substantially similar halves pivotally connected together at a living hinge, and the method further includes separating the two sleeve halves to decouple the valve holder from the sleeve. Alternatively, the packaging sleeve comprises at least two components, one of the components being a generally planar clip and the other component circumscribing the clip and extending substantially the entire axial height of the jar between the bottom and the lid, whereby the method includes removing the assembly of the valve, holder and packaging sleeve from the jar using the shaft. In one embodiment, the leaflet parting member includes threads that engage mating threads on the valve holder, and the method including providing structure in the jar that prevents rotation of the valve holder relative to the jar in at least one direction.

In accordance with one aspect of the application, an exemplary packaging sleeve formed from a single molded component for securing a prosthetic heart valve within a jar comprises a generally planar clip having a peripheral edge and an entry slot leading therefrom to a central docking aperture wider than the entry slot. The clip is defined by two substantially similar halves pivotally connected together at a living hinge at the peripheral edge of the clip opposite from the entry slot. A plurality of lower legs extend downward from the clip and elevate the clip above and generally parallel to a flat surface on which the sleeve is placed. A plurality of upstanding posts having longer lengths than the legs project upward from the clip, at least one post being provided on each of the two halves of the clip. The clip halves are generally semi-circular with contoured inner edges defining the entry slot, the entry slot forming an increasing gap from the docking aperture radially outward. In one embodiment, there are two upstanding posts that project upward from the peripheral edge of the clip at locations that are approximately diametrically opposite around the clip. The upstanding posts extend upward from the clip at a height between about 60-80% of the overall axial sleeve height.

The assembly can further include a plurality of axial ribs extending upward from the clip, at least some of which are distributed around an approximately semi-circular reinforcing wall. Alternatively, the axial ribs extend upward from the clip and emanate generally radially from the central docking aperture. In one embodiment, each of the upstanding posts extends upward adjacent the peripheral edge of the clip and includes a main wall portion having a slight curvature generally tracking the peripheral edge, and an axial reinforcing rib projecting outward from the main wall portion. Further, each of the lower legs extends downward from the peripheral edge of the clip and includes a main wall portion with a slight curvature conforming to the peripheral edge, and an axial rib projecting outward from the main wall portion.

Another packaged prosthetic heart valve assembly disclosed herein includes a jar having a closed bottom and a lid, a prosthetic heart valve having an inflow end and an outflow end, a valve holder attached to the outflow end of the valve, and a packaging sleeve formed from a single molded component and sized to fit closely within the jar. The packaging sleeve has a generally planar clip with a peripheral edge and an entry slot leading therefrom to a central docking aperture wider than the entry slot. A plurality of lower legs extend downward from the clip and elevate the clip above and generally parallel to the jar bottom. A plurality of upstanding posts having longer lengths than the legs project upward from the clip into proximity with the jar lid, wherein the valve holder couples to the central docking aperture of the clip such that the holder is oriented toward but elevated from the bottom of the jar. In the aforementioned assembly, the clip may be defined by two substantially similar halves pivotally connected together at a living hinge at the peripheral edge of the clip opposite from the entry slot.

A further packaged prosthetic heart valve assembly of the present application features a jar having a closed bottom and a lid, a prosthetic heart valve having an inflow end and an outflow end, a valve holder attached to the outflow end of the valve, and a packaging sleeve. The packaging sleeve has a generally circular periphery as seen from above that fits closely within the jar and an axial dimension that extends substantially the entire axial height of the jar between the bottom and the lid. The packaging sleeve further includes a generally planar clip that extends radially across the interior of the jar substantially closer to the jar bottom than to the lid. The clip has an entry slot extending from a peripheral edge to a central docking aperture wider than the entry slot. The valve holder couples to the central docking aperture of the clip such that the holder is oriented toward the bottom of the jar.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

The invention will now be explained and other advantages and features will appear with reference to the accompanying schematic drawings wherein:

FIG. 5 is a perspective view of the packaging sleeve of FIGS. 1 and 2;

FIGS. 6A-6G are various elevational, plan, and sectional views of the packaging sleeve of FIG. 5;

FIGS. 7-8D are perspective, elevational, and plan views of an exemplary heart valve holder used with the packaging sleeve described herein;

FIGS. 9A-9C shows several steps in a process for coupling a leaflet parting member to a heart valve holder braced by the packaging sleeve within the storage and shipping jar;

FIGS. 10A-10C show several steps in the removal of a heart valve/holder combination from the packaging sleeve;

FIGS. 11A and 11B illustrate steps in coupling a valve delivery tube to the leaflet parting member and removal of a handle thereof, and FIG. 11C illustrates an exemplary coupling between a parting member and an elongated shaft;

FIGS. 12A and 12B show two steps in an alternative process for removing a heart valve/holder combination from the packaging sleeve using the valve delivery tube;

DETAILED DESCRIPTION OF THE PREFERRED EMBODIMENTS

The present invention provides an improved packaging system for prosthetic heart valves that effectively stabilizes the valve within a storage and shipping jar, and permits coupling of a leaflet parting member to the valve for use in a delivery procedure. The leaflet parting member is particularly useful for an exemplary hybrid prosthetic aortic valve having an expandable coupling stent thereon. However, other uses for the leaflet parting member are contemplated, such as to provide access to a distal side of the prosthetic heart valve during the actual implant steps. Moreover, the improved packaging system enables a prosthetic aortic valve to be stored within the jar with its holder pointing down, which may prove advantageous in other contexts.

Because of the drawbacks associated with conventional open-heart surgery, percutaneous and minimally-invasive surgical approaches are garnering intense attention. In one technique, an expandable prosthetic valve is configured to be implanted in a much less invasive procedure by way of catheterization. More recently, expandable valves are delivered through direct-access ports introduced through the chest. Another promising technique is a hybrid non-expandable valve with an expandable stent thereon which, though still requiring cardiopulmonary bypass, can be implanted in a much shorter time frame.

Figure 2:
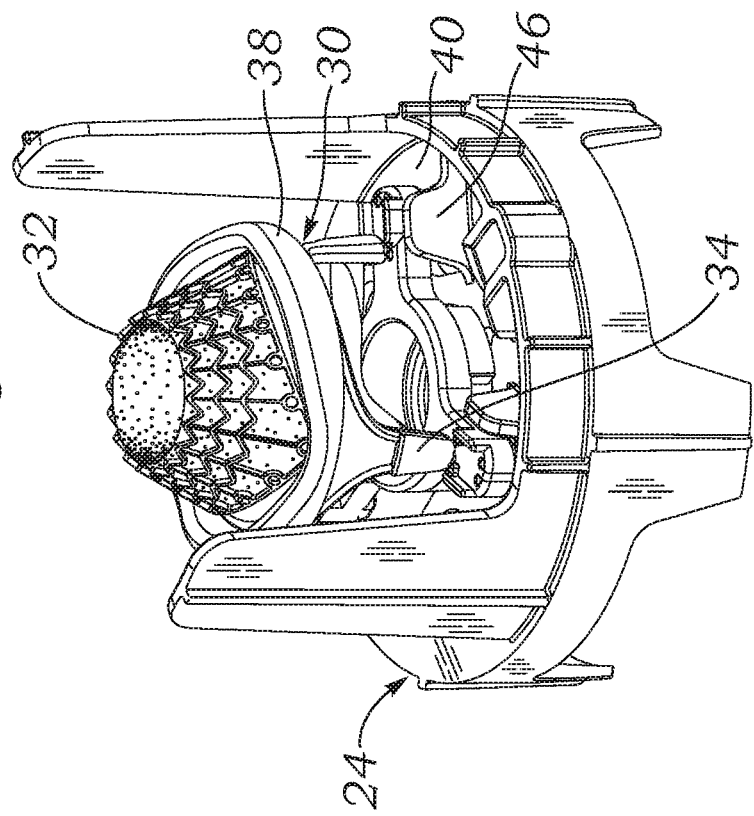
FIGS. 1 and 2 are perspective views from front and back of an assembly of a prosthetic heart valve attached to a holder and positioned within a packaging sleeve.
Figure 1:
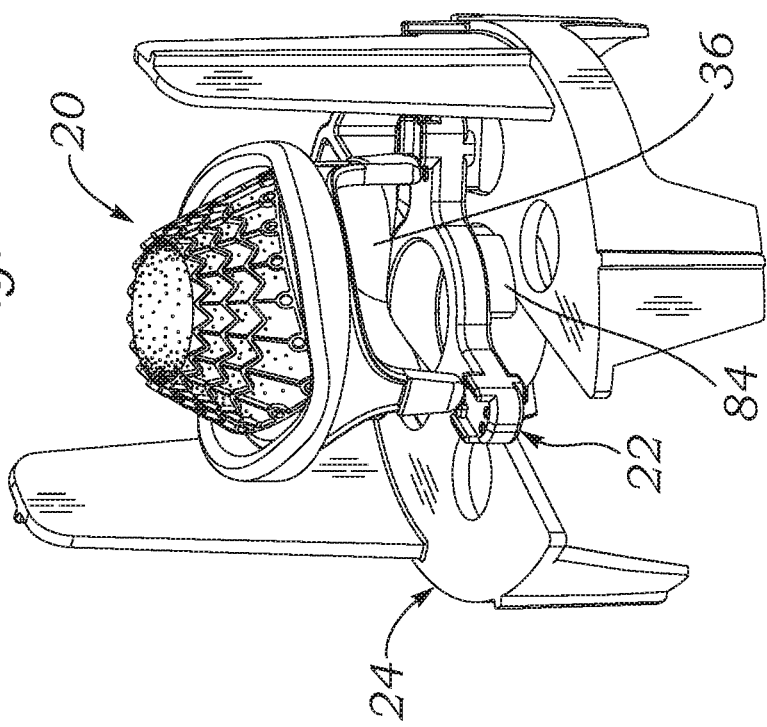
Figure 3:
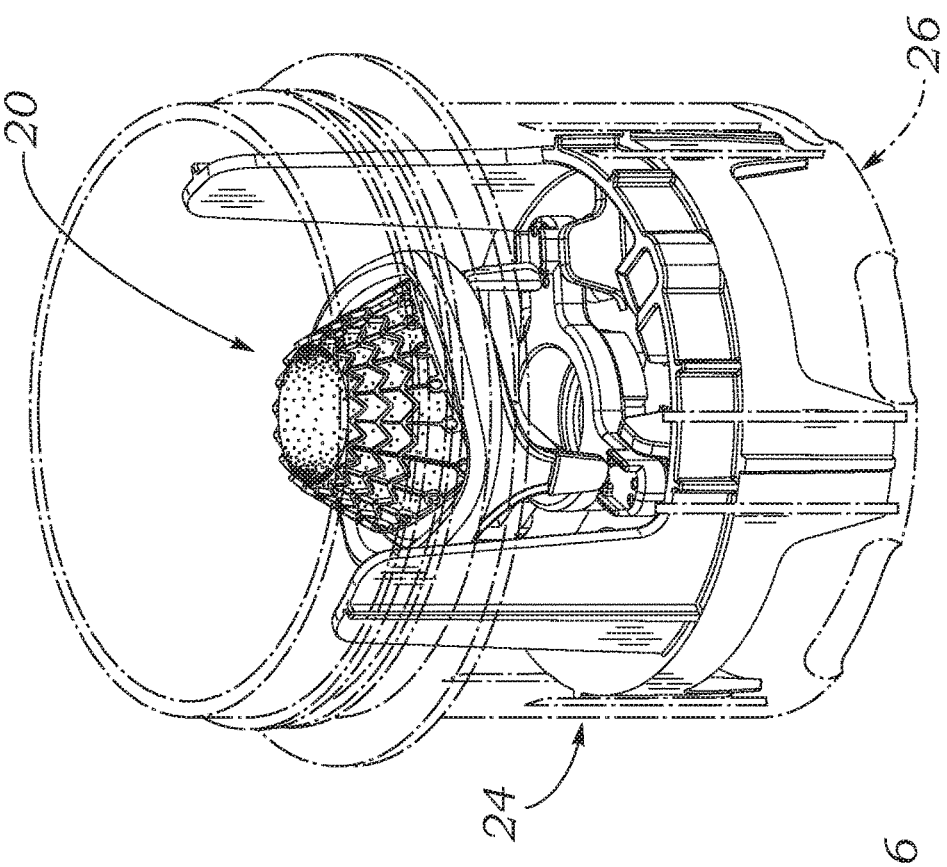
FIGS. 3 and 4 are perspective views of the assembly of FIGS. 1 and 2 positioned within a storage and shipping jar (without a lid) shown in phantom.
Figure 4:
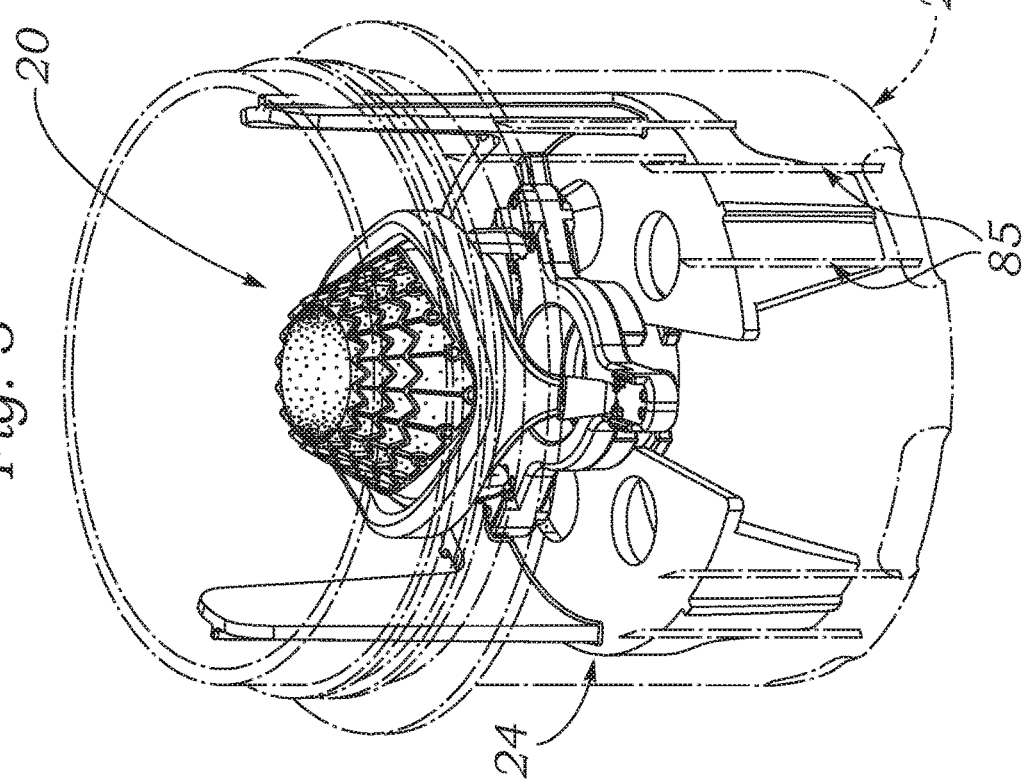

FIGS. 1 and 2 are front and back perspectives of an assembly of a hybrid prosthetic heart valve 20 attached to a holder 22 and mounted to a packaging sleeve 24. FIGS. 3 and 4 show the assembly of FIGS. 1 and 2 positioned within a storage and shipping jar 26 (without a lid) in phantom. As will be explained below, the packaging sleeve 24 provides a number of significant benefits particularly useful for the hybrid prosthetic heart valve 20 disclosed. In an exemplary embodiment, packaging sleeve 24 is a single, unitary component, preferably molded plastic. However, as will be seen below, a packaging sleeve having more than one part is entirely possible and encompassed by the present application.

Additionally, the particular prosthetic heart valve 20 disclosed includes bioprosthetic leaflets which are typically stored in a preservative solution, such as glutaraldehyde. Therefore the packaging sleeve 24 fits closely within the fluid tight shipping jar 26 which is then sealed with a suitable lid (not shown). However, certain features of the exemplary heart valve and delivery system may be adapted for valves that do not require storage in a fluid preservative, and instead may use a dry sterile jar. The invention should therefore not be considered limited to a valve packaging system having a fluid preservative.

The illustrated prosthetic heart valve 20 is considered a hybrid type because it has a non-expandable, non-collapsible valve member 30 and an expandable coupling stent 32 attached to and projecting from a distal end of the valve member 30. The valve member 30 may take a variety of forms, but preferably includes a cloth-covered wireform that follows an undulating path around the periphery of the valve with alternating cusps (not numbered) and commissure posts 34. A plurality of flexible leaflets 36 extend across a generally circular orifice defined within the valve member 30, each of which receives peripheral support along the wireform, in particular by two adjacent commissure posts 34. An annular, preferably contoured, sewing ring 38 circumscribes the valve 20 at an axial location approximately between the valve member 30 and expandable coupling stent 32.

The term "valve member" refers to that component of a heart valve that possesses the fluid occluding surfaces to prevent blood flow in one direction while permitting it in another. Various constructions of valve members are available, including those with flexible leaflets and those with rigid leaflets, or even a ball and cage arrangement. The leaflets may be bioprosthetic, synthetic, metallic, or other suitable expedients.

When used for aortic valve replacement, the valve member 30 preferably has three flexible leaflets 36 which provide the fluid occluding surfaces to replace the function of the native valve leaflets. In various preferred embodiments, the valve leaflets may be taken from another human heart (cadaver), a cow (bovine), a pig (porcine valve) or a horse (equine). In other preferred variations, the valve member may comprise mechanical components rather than biological tissue. The three leaflets are supported by the internal wireform, which typically include a synthetic (metallic and/or polymeric) support structure of one or more components covered with cloth for ease of attachment of the leaflets.

In a particularly preferred embodiment, the prosthetic valve 20 comprises a commercially available, non-expandable prosthetic valve member 30, such as the Carpentier-Edwards PERIMOUNT Magna® Aortic Heart Valve available from Edwards Lifesciences. In this sense, a "commercially available" prosthetic heart valve is an off-the-shelf (i.e., suitable for stand-alone sale and use) prosthetic heart valve defining therein a non-expandable, non-collapsible support structure and having a sewing ring capable of being implanted using sutures through the sewing ring in an open-heart, surgical procedure.

The coupling stent 32 is preferably plastically-expandable, and in its radially constricted (crimped) or undeployed state assumes a conical inward taper in the distal direction, converting to an oppositely flared shape in its deployed state. The coupling stent 32 may be a pre-crimped, tapered, 316 L stainless steel balloon-expandable stent, desirably covered by a polyester skirt to help seal against paravalvular leakage and promote tissue ingrowth once implanted within the annulus. The coupling stent 32 preferably has an axial length as great as or greater than that of the valve member 30. Anchoring devices such as barbs or other protuberances from the coupling stent 32 may be provided to enhance the frictional hold between the coupling stent and the annulus. The coupling stent 32 preferably attaches to the ventricular (or inflow) aspect of the valve's sewing ring 38 during the manufacturing process in a way that preserves the integrity of the sewing ring and prevents reduction of the valve's effective orifice area (EOA). Desirably, the coupling stent 32 will be continuously sutured to the sewing ring 38 in a manner that maintains the outer contours of the sewing ring.

For definitional purposes, the terms "stent" or "coupling stent" refer to a structural component of a heart valve that is capable of attaching to tissue of a heart valve annulus. The coupling stent 32 described herein may be tubular, have varying shapes or diameters. Other coupling stents that could be used with valves of the present invention include rigid rings, spirally-wound tubes, and other such tubes that fit tightly within a valve annulus and define an orifice therethrough for the passage of blood.

By utilizing an expandable stent 32 coupled to a non-expandable valve member 30, the duration of the implant operation is greatly reduced as compared with a conventional sewing procedure utilizing an array of sutures. The expandable stent 32 may simply be radially expanded outward into contact with the implantation site, or may be provided with additional anchoring means, such as barbs. This provides a rapid connection means as it does not require the time-consuming process of suturing the valve to the annulus. The operation may be carried out using a conventional open-heart approach and cardiopulmonary bypass. In one advantageous feature, the time on bypass is greatly reduced due to the relative speed of implanting the expandable stent.

As a point of further definition, the term "expandable" is used herein to refer to a component of the heart valve capable of expanding from a first, delivery diameter to a second, implantation diameter. An expandable structure, therefore, does not mean one that might undergo slight expansion from a rise in temperature, or other such incidental cause such as fluid dynamics acting on leaflets or commissures. Conversely, "non-expandable" should not be interpreted to mean completely rigid or dimensionally stable, merely that the valve member is not expandable/collapsible like some proposed minimally-invasively or percutaneously-delivered valves, and some slight expansion of conventional "non-expandable" heart valves, for example, may be observed.

Certain features of an exemplary hybrid coupling stent and valve member are described in U.S. Provisional Application Nos. 61/139,398, filed Dec. 19, 2008, and 61/220, 968, filed Jun. 26, 2009, the contents of which are expressly incorporated herein. These provisional applications disclose both "two-stage" and unitary prosthetic valves, although it is the unitary prosthetic valves that derive the most benefit from being coupled with the improved packaging system disclosed herein.

In the description that follows, the term "body channel" is used to define a blood conduit or vessel within the body. Of course, the particular application of the prosthetic heart valve determines the body channel at issue. An aortic valve replacement, for example, would be implanted in, or adjacent to, the aortic annulus. Likewise, a mitral valve replacement will be implanted at the mitral annulus. Certain features of the present invention are particularly advantageous for one implantation site or the other, in particular the aortic annulus. However, unless the combination is structurally impossible, or excluded by claim language, any of the heart valve embodiments described herein could be implanted in any body channel.

FIG. 5 is a perspective view, and FIGS. 6A-6G are various other views of the packaging sleeve 24 of FIGS. 1 and 2. The packaging sleeve 24 has a circular periphery as viewed in plan view of FIGS. 6B and 6C, with a planar platform or clip 40 axially separating a plurality of lower legs 42 from a pair of upstanding posts 44 and a plurality of shorter ribs 46. The circular periphery of the sleeve 24 fits closely within the inner diameter of the jar 26, while the axial height fits closely within the axial inner dimension of the jar 26. In this manner, the confines of the jar 26 constrain the sleeve 24 from movement when placed therein.

The clip 40 desirably lies in a plane perpendicular to the axis of the circular periphery of the sleeve 24, and includes a pair of generally semi-circular halves 50a, 50b joined at a living hinge 52, as seen best in FIGS. 6B and 6C. As will be explained below, the living hinge 52 permits the two halves 50a, 50b to pivot apart from one another. Contoured inner edges of the two halves 50a, 50b define an entry slot 54 leading to a generally circular docking aperture 56 preferably centered in the sleeve 24. The entry slot 54 defines a slightly increasing gap from the docking aperture 56 radially outward. The two halves 50a, 50b converge toward each other at a neck 58 separating the docking aperture 56 from a relief region 60. The halves 50a and 50b desirably do not contact at the neck 58 for sterility reasons and to facilitate removal of the bio-prosthesis 20 from the sleeve 24.

There are desirably at least two of the upstanding posts 44, although more than two may be provided. The posts 44 extend upward adjacent a peripheral edge of the clip 40 a majority of the axial height of the packaging sleeve 24, and preferably extend between about 60-80% of the overall sleeve height. When held therein, the prosthetic heart valve 20 is inverted above the clip 40 and within the confines of the posts 44, so as to be protected from inadvertent damage upon removal from the jar 26. However, the smooth, tapered shape of the posts 44, and the presence of a large circumferential space surrounding the entry slot 54 facilitates removal of the valve/holder. In a preferred embodiment, there are two upstanding posts 44 located approximately diametrically opposite across the clip 40. Preferably, the sleeve 24 includes a plurality of axial ribs 61 that enhance the structural integrity thereof for better handling during packaging and valve retrieval. Each of the upstanding posts 44 includes a main wall portion that conforms generally to a circular curvature and an axial reinforcing rib 61 projecting outward therefrom. Other ribs 61 extend up each post 44, while others are distributed around an approximately semi-circular reinforcing wall 63, which also serves to structurally rigidify the sleeve 24. The ribs 61 also help to prevent warping during the molding process.

The packaging sleeve 24 preferably includes four of the lower legs 42, although more or less than four may be utilized. In the illustrated embodiment, the four legs 42 are generally evenly spaced around the lower circumference of the clip 40 and taper slightly inward from upper to lower ends thereof. As seen in FIG. 5, legs 42 are axially or vertically oriented and each has a main wall portion with a slight curvature conforming to the outer periphery of the clip 40. In this configuration, the legs 42 closely conform to the inner wall of the shipping jar 26. Each leg 42 further includes an outwardly-projecting axial rib 62 that interacts with the inner wall of the shipping jar 26, as will be explained. The legs 42 extend downward and elevate the clip 40 above and generally parallel to bottom of the jar 26, as seen in FIGS. 3 and 4. In this way, the holder 22 may extend below the clip 40 though not touch the jar bottom. Furthermore, a Serial No. ID tag secured to the prosthetic heart valve 20 via a suture may be deposited within the volume created by the legs 42 underneath the clip 40. This helps prevent contact of the ID tag with the valve leaflets, which could potentially cause damage thereto. Moreover, depositing the ID tag under the clip 40 when assembling the valve package in the jar is a relatively simple step, as opposed to some earlier designs which required the tag to be held around the outside of the packaging sleeve while it was inserted into the jar.

FIGS. 7-8D show an exemplary heart valve holder 22 used with the packaging sleeve 24 that comprises a proximal tubular hub 70 forming a central portion of the holder and three legs 72 circumferentially equidistantly spaced and projecting radially outward therefrom. The legs 72 comprise inner struts 74 and outer commissure rests 76. The valve member 30 includes a plurality, typically three, commissures 34 (FIG. 1) that project in an outflow direction. A seen in FIG. 8C, the commissure rests 76 preferably incorporate receptacles 78 into which fit the tips of the commissures 34. Per convention, the holder 22 has a series of through holes 80 in the legs 72 permitting connecting sutures to be passed through fabric in the valve member 30 and across a proximal cutting guide 82 in each leg. As is known in the art, severing a middle length of suture that is connected to the holder 22 and passes through the valve permits the holder to be pulled free from the valve when desired.

The exemplary holder 22 further includes several features that permit it to couple with the prosthetic heart valve 20, packaging sleeve 24, and with a delivery system, as will be described. The commissure rests 76 having suture holes 80 therein for mating with the valve commissures 34 have been described. In addition, the hub 70 includes a series of outwardly directed interrupted lugs 84 that help the holder 22 mate with the clip 40 of the packaging sleeve 24. In the illustrated embodiment, there are six separate lugs 84 arranged in three axially spaced pairs, as best seen in FIG. 7. Each pair of lugs 84 defines therebetween a channel that receives the inner edge of the docking aperture 56, as seen in FIG. 6C. The external diameter of the tubular hub 70 is sized the same as or slightly smaller than the inner diameter of the docking aperture 56 to provide some clearance therebetween, and is larger than the opening defined by the entry slot 54 to ensure holder 22 is retained within aperture 56.

FIGS. 1 and 2 (and with reference to FIG. 6C) illustrate the holder 22 of FIG. 7 positioned in the docking aperture 56, wherein the lugs 84 are positioned above and below the planar clip 40 (providing a clearance fit). The hub 70 fits within the docking aperture 56 with some clearance. The distributed lugs 84 project above and below the planar clip 40 and thus fix the axial position of the holder 22, and valve 20 thereon, with respect to the packaging sleeve 24. From FIG. 6C, it can be seen that the tubular hub 70 will be secured centrally in the docking aperture 56 of the packaging sleeve 24 by the narrower entry slot 54. As will be described below, the two halves 50a, 50b of the packaging sleeve 24 can pivot away from one another about the living hinge 52, but when the sleeve is positioned in the jar 26 the sidewalls constrain the two halves 50a, 50b in the closed position of FIG. 6C, and therefore the holder 22 and valve thereon is held in a fixed centralized position. Desirably, the sleeve 24 and the jar 26 are designed with a clearance fit for sterility assurance reasons.

FIGS. 3 and 4 illustrate an advantageous cooperation between the packaging sleeve 24 and jar 26 which limits relative rotation therebetween. Specifically, the aforementioned outwardly-projecting axial ribs 62 radially overlap with axial rails 85 formed on the inner wall of the shipping jar 26. The interference between the ribs 62 on the packaging sleeve 24 and axial rails 85 on the jar 26 limits the total axial rotational freedom of the sleeve. In particular, the extent of rotation permitted is approximately equal to the angular spacing of the axial rails 85, which is preferably between about 5-20°, more preferably between about 5-10°. This anti-rotation feature restricts the rotational movement of the valve during distribution to customers as well as facilitates the attachment of a deployment tool to the valve. That is, as will be described below, a tool threads on to the holder while in the jar to lift out the valve/holder sub-assembly and packaging sleeve, and the anti-rotation feature thus provide a reaction force to enable the parts to be coupled without simply spinning the sleeve within the jar. Moreover, placing the interacting ribs 62 and rails 85 on the radial walls of the two parts permits the technician to engage the tool to the valve holder in various orientations of the jar, even inverted, which was not the case with earlier designs with the anti-rotation feature on the bottom of the jar.

The one-piece design of the packaging sleeve 24 eliminates complexity involved with packaging assembly process, which also reduces manufacturing process errors. The design will provide stream-lined access and aseptic presentation of the valve package in operating rooms and reduce surgery time at the customer's end as well. Furthermore, the design reduces the number of components to be maintained in the manufacturer's inventory and also that need to be disposed at customer's end. Additionally, the use of only two posts for valve protection instead of a traditional clip/tubular sleeve assembly reduces the number of steps (lesser number of components) used for producing these parts, resulting in possible cost and energy savings.

One procedure for packaging the valve 20 includes sliding the valve holder 22 in to the entry slot 54 of the clip 40 to lock it in place with the valve projecting upward between the posts 44. The packaging sleeve 24 with valve/holder sub-assembly is inserted into the jar so that the anti-rotation ribs 62 align with the rails 85 of the jar. The jar is filled with a liquid sterilant such as glutaraldehyde, a jar lid is attached, and a heat shrink sleeve applied to the lid/jar boundary. Finally, the entire package is sterilized.

The holder 22 of FIG. 7 further includes internal threading 86 within the tubular hub 70 that mates with external threading on an element of a delivery system. FIGS. 9A-9C show several steps in a process for coupling a leaflet parting member 100 of a valve delivery system to the holder 22. The parting member 100 comprises a short tubular member having a stepped diameter with an externally-threaded narrower distal portion 102 and a wider proximal portion 104 with no threads. The parting member 100 couples to an elongated shaft 106 via mating threading, a snap lock, bayonet lock, a simple interference fit, or other quick-release coupling (an exemplary configuration is seen in FIG. 11C).

As depicted in FIG. 9A, the elongated shaft 106 has sufficient length to deliver the parting member 100 on its distal end into the jar 26 and through the valve 20 to the holder 22. FIGS. 9B and 9C illustrate the coupling operation with the sleeve 24 and jar 26 removed for clarity. It should be understood that although the parting member 100 is desirably coupled to the holder 22 while it remains in the jar 26, the entire assembly of the packaging sleeve 24 and valve/holder may be first removed from the jar 26 by hand or forceps. However, the reader can assume that the steps shown in FIGS. 9B and 9C are performed with the assembly still in the jar 26.

A technician advances the parting member 100 on the end of the shaft 106 through the conical coupling stent 32 and within the valve member 30. Since the valve leaflets 36 are angled inward from the inflow to the outflow direction (downward in the drawings), the parting member 100 easily passes therebetween in the same direction, in the process displacing the leaflets outward. Ultimately, the technician advances the parting member 100 far enough into contact with the holder 22, and screws the external threads on the distal portion 102 into the internal threads on the tubular hub 70. Note in FIG. 2 the rotational stability provided to the holder 22 by the short ribs 46 on the packaging sleeve clip 40, which prevents rotation of the holder during this engagement. The short ribs 46 emanate generally radially, and preferably at 120° spacing, from the central docking aperture 56 so as to align with and thus prevent rotation of the outwardly radiating legs 72 of the holder 22.

The final position of the parting member 100 coupled to the holder 22 is shown in FIG. 9C, with a length of the threaded distal portion 102 projecting from the hub 70. Note the valve leaflets 36 outwardly displaced by the proximal portion 104 of the parting member 100. The primary purpose of the parting member 100 is to open the leaflets 36 and provide a throughbore for passage of an expander, such as a balloon on the end of a catheter, for expanding the coupling stent 32. Without the parting member 100, attempted passage of a balloon catheter, for instance, in the direction opposite to that which the leaflets 36 extend my damage the leaflets. That is, as seen from the outflow end of the valve 20, the free edges of the leaflets 36 come together, or coapt, in a trefoil configuration, effectively closing the orifice. Passing any instrument backwards through the leaflets 36 can either damage the leaflets or invert them so as to be implanted improperly.

Is important also to note that parting member 100 desirably couples to the holder 22 and displaces the leaflets 36 outward just before an implant procedure, typically in the operating theater. Although the parting member 100 could be pre-assembled to the holder 22 and stored and shipped with the valve/holder assembly in the jar 26, this is not advisable. Desirably, the bioprosthetic leaflets 36 remain in their closed or coapted position during what sometimes can be a very lengthy storage duration. In this way, the tissues of the leaflets 36 remain relaxed in the valve closed position, which is believed to enhance performance after implantation. Any deformation of the leaflets from long-term storage in an open position could result in regurgitation or other problems. Coupling the parting member 100 with the holder 22 during storage duration might detrimentally deform the leaflets and affect the valve performance.

As mentioned, the parting member 100 couples to the holder 22 while in the jar 26. FIGS. 10A-10C illustrate a subsequent procedure for removal of the heart valve/holder combination from the packaging sleeve 24, using the parting member 100 and attached shaft 106. First, the technician removes the entire assembly from within the jar 26, as seen in FIG. 10A. It should be noted that the valve member 30 remains surrounded and thus protected by elements of the packaging sleeve 24, in particular the planar clip 40 and upstanding posts 44. Moreover the elongated shaft 106 enables the technician to manipulate the assembly remotely without having to resort to grasping the packaging sleeve 24 with fingers or forceps, for example.

At this stage, the technician has two options: detach the valve/holder assembly from the packaging sleeve 24, or first attach a second component of the valve delivery system. The latter option is disclosed in FIGS. 10B-10C and 11A-11B, but it should be understood that the specific sequence of steps can be varied, as will be explained.

As one option, the technician first removes the valve 20 and holder 22 from the packaging sleeve 24, as seen in FIGS. 10B and 10C. The packaging sleeve 24 facilitates this removal by virtue of the ability of the two halves 50a, 50b to pivot away from one another about the living hinge 52. In this sense, the living hinge 52 ensures that the packaging sleeve 24 will flex while being packaged and also during valve retrieval without breaking. It should be understood that once the packaging sleeve 24 is removed from the jar 26 there is very little to prevent the two halves 50a, 50b from separating, other than the relatively low stiffness of the living hinge 52 and the friction between the contacting parts. Consequently, the technician can easily radially displace the valve/holder combination toward the entry slot 54 and out of the docking aperture 56, thus forcing the two halves 50a, 50b apart. Of course, this operation may be helped along by manually separating the two halves 50a, 50b, and indeed the technician could hold the valve/holder combination stationary while removing the packaging sleeve 24 from around it. The assembly of the valve 20, holder 22, parting member 100 and shaft 106 can be seen in FIG. 11A.

FIGS. 11A and 11B show a valve delivery tube 110 being coupled to the leaflet parting member 100, and subsequent removal of the elongated shaft 106. The delivery tube 110 comprises an elongated hollow shaft 112 having a proximal coupler 114 and a distal coupler 116. The distal coupler 116 includes internal threads that mate with the external threads on the narrower portion 102 of the leaflet parting member 100, as shown in FIG. 11C. The distal coupler 116 threads onto the narrower portion 102 until it abuts the proximal end of the tubular hub 70 of the valve holder 22. Subsequently, the elongated shaft 106 may be removed from the distal end of the parting member 100, as seen in FIG. 11B. Again, this can be accomplished through mating threading, a bayonet lock, etc, though in the illustrated embodiment the shaft 106 is simply pulled straight off of the parting member 100. More particularly, the wider proximal portion 104 of the parting member 100 provides a series of axial grooves 120 which receive axial ribs 122 on the shaft 106. The ribs 120 fit snugly in the axial grooves 124 in an interference fit, and transfer torque between the two elements.

Ultimately, the valve delivery tube 110 provides a convenient handle for manipulating the prosthetic valve 20 on its holder 22. Note that the leaflet parting member 100 remains in place displacing the leaflets 36 outward. Although not shown, the inner diameter of the hollow shaft 112 desirably matches the inner diameter of the parting member 100 to provide a continuous and substantially uninterrupted throughbore from the proximal coupler 114 through the parting member, and distally beyond the leaflets 36. This continuous throughbore facilitates passage of an expander, such as a balloon on the end of a catheter, through the valve leaflets 36 and within the coupling stent 32.

As mentioned above, another option is to couple the valve delivery tube 110 to the parting member 100 with the valve/holder assembly still in the packaging sleeve 24. FIGS. 12A and 12B show a configuration where the valve delivery tube 110 has been coupled in this manner to the parting member 100 (not shown), with the packaging sleeve 24 still attached to the holder 22. The same procedure described above for removing the elongated shaft 106 can be performed leaving just the valve delivery tube 110 connected to the parting member 100, as shown. In this configuration, the valve 20 remains protected by the clip 40 and posts 44 of the packaging sleeve 24. The figures again show easy removal of the valve/holder assembly from the packaging sleeve 24 by virtue of the bifurcated configuration of the sleeve at the living hinge 52. Once removed from the packaging sleeve 24, the valve delivery tube 110 can be coupled to other elements in the delivery system, with the prosthetic heart valve 20 prepared on the distal end thereof for deployment.

Figure 13:
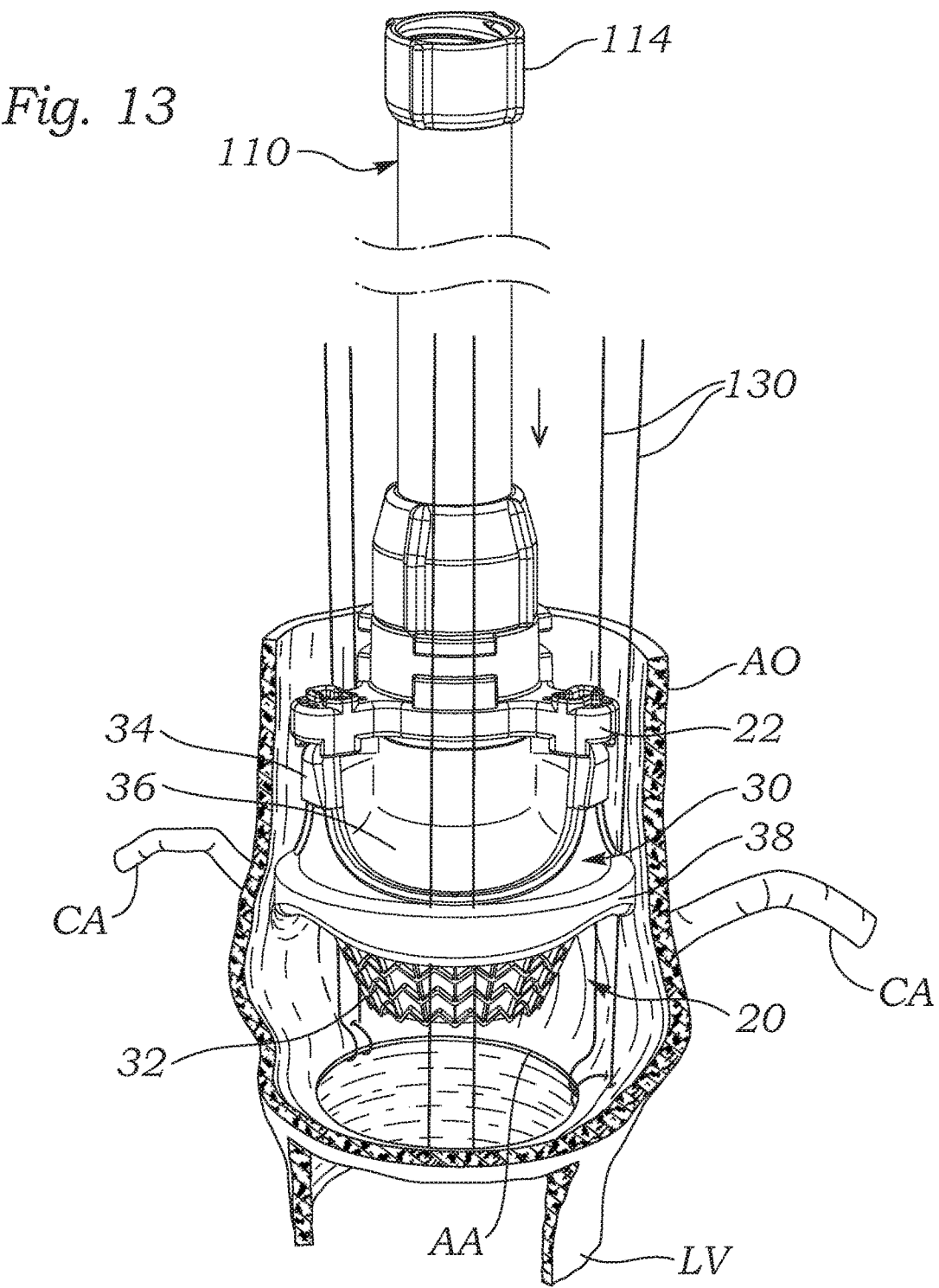
FIG. 13 illustrates delivery to an aortic annulus of an exemplary heart valve/holder combination using the valve delivery tube.

FIG. 13 illustrates a snapshot in the process of delivering the heart valve 20 to an aortic annulus AA using the valve delivery tube 110. For purpose of orientation, the heart valve 20 has an inflow end down and an outflow end up, and the terms proximal and distal are defined from the perspective of the surgeon delivering the valve inflow end first. Thus proximal is synonymous with up or outflow, and distal with down or inflow.

The aortic annulus AA is shown schematically isolated and it should be understood that various anatomical structures are not shown for clarity. The annulus AA includes a fibrous ring of tissue that projects inward from surrounding heart walls. The annulus AA defines an orifice between the ascending aorta AO and the left ventricle LV. Although not shown, native leaflets projecting inward at the annulus AA to form a one-way valve at the orifice. The leaflets may be removed prior to the procedure, or preferably left in place and outwardly compressed by the expandable coupling stent 32. If the leaflets are removed, some of the calcified annulus may also be removed, such as with a rongeur. The ascending aorta AO commences at the annulus AA with three outward bulges or sinuses, two of which are centered at coronary ostia (openings) leading to coronary arteries CA. As will be seen below, it is important to orient the prosthetic valve 20 so that the commissure posts 34 are not aligned with and thus not blocking the coronary ostia.

FIG. 13 shows a plurality of pre-installed guide sutures 130. The surgeon attaches the guide sutures 130 at three evenly spaced locations around the aortic annulus AA. In the illustrated embodiment, the guide sutures 130 attach to locations below or corresponding to the nadirs of the native cusps (that is, two guide sutures are aligned with the coronary sinuses, and the third centered below the non-coronary sinus). The guide sutures 130 are preferably looped twice through the annulus AA from the outflow or ascending aorta side to the inflow or ventricular side. Of course, other suturing methods or pledgets may be used depending on surgeon preference.

The guide sutures 130 extend in pairs of free lengths from the annulus AA and out of the operating site. The prosthetic heart valve 20 mounts on the distal end of the delivery handle 110 and the surgeon advances the valve into position within the aortic annulus AA along the guide sutures 130. That is, the surgeon threads the three pairs of guide sutures 130 through evenly spaced locations around the suture-permeable ring 38. If the guide sutures 130, as illustrated, anchor to the annulus AA below the aortic sinuses, they thread through the ring 38 mid-way between the valve commissure posts 34, in particular at cusp regions of the sewing ring that are axially thicker than the commissure locations.

FIG. 13 illustrates the dual nature of the valve delivery tube 110 in that it provides both a portion of the handle of the delivery system, as well as a through lumen that leads directly through the holder 22 and leaflet parting member 100 (not shown) to the space within the coupling stent 32. Although not shown, other elements of the delivery system mate with the proximal coupler 114 to provide an elongated access channel for delivery of the expander such as a balloon to within the coupling stent 32.

The surgeon advances the heart valve 20 until it rests in a desired implant position at the aortic annulus AA. The suture-permeable ring 38 desirably contacts the aortic side of the annulus AA, and is thus said to be in a supra-annular position. Such a position enables selection of a larger orifice prosthetic valve 20 in contrast to placing the ring 38, which by definition surrounds the valve orifice, within the annulus AA, or infra-annularly. Further details of a similar delivery procedure are shown and described in U.S. Provisional Application No. 61/220,968, filed Jun. 26, 2009, the contents of which are expressly incorporated herein.

At this stage, the coupling stent 32 is expanded, such as with a balloon, to anchor the prosthetic heart valve 20 to the aortic annulus AA and seal a concentric space between aortic annulus/LVOT and bio-prosthesis to prevent paravalvular leaks. The operator then severs any retention sutures between the holder 22 and valve 20, deflates the balloon and withdraws it along with the entire assembly of the leaflet parting member 100, holder 22 and valve delivery tube 110. Finally, the guide sutures 130 have been tied off to further secure the valve in place.

Figure 14B:
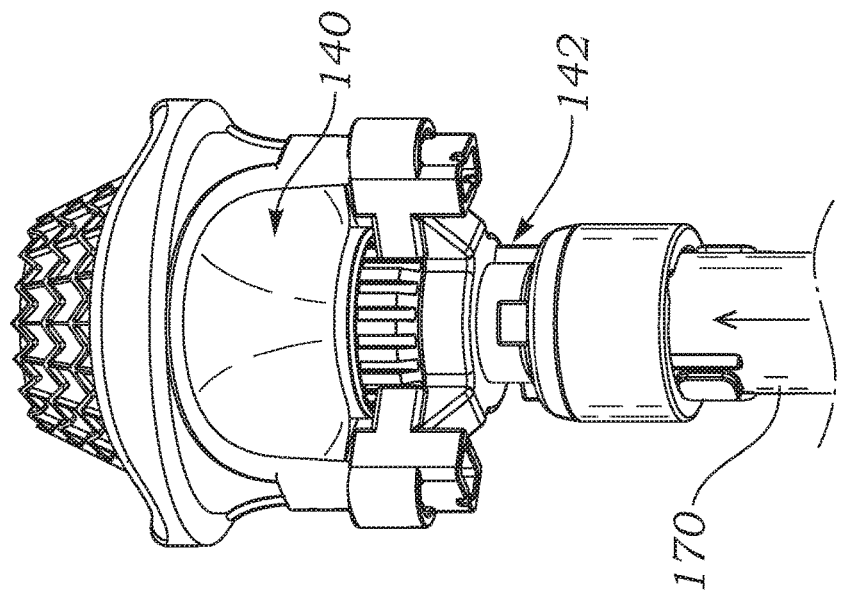
FIGS. 14A and 14B are perspective views showing coupling of an alternative leaflet parting member and valve delivery tube to a heart valve/holder combination.
Figure 14A:
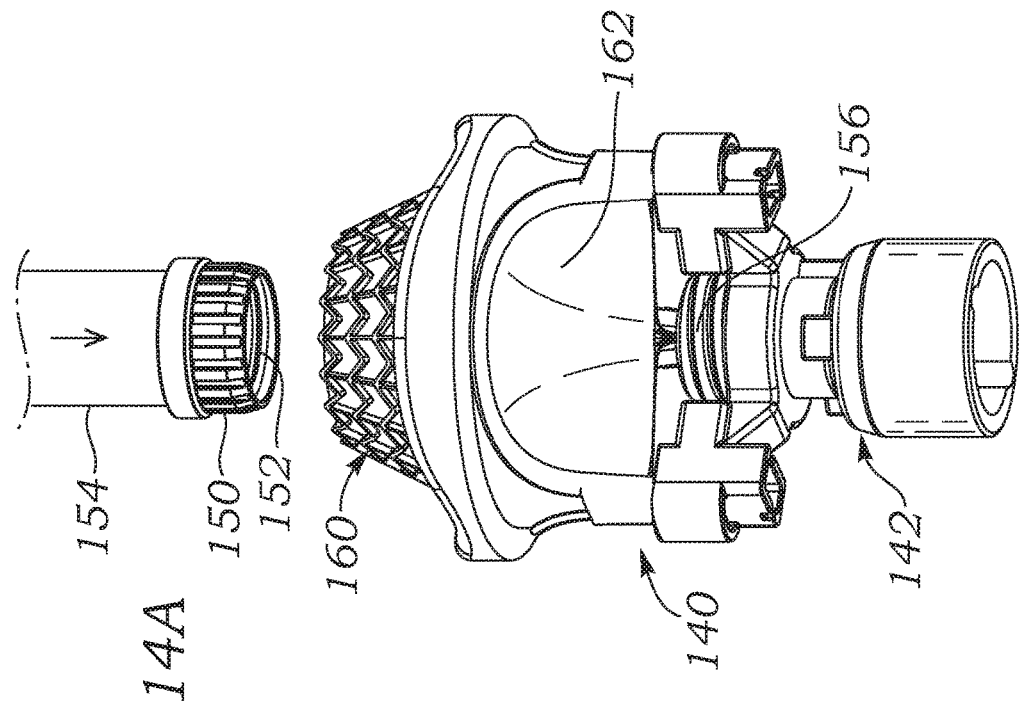

FIGS. 14A and 14B are perspective views showing an alternative holder/delivery system configuration for a prosthetic valve 140. Although not shown, the prosthetic valve 140 along with its holder 142 are preferably retained within the aforementioned packaging sleeve 24 and within the shipping jar 26, with the holder 142 down in the jar. In this embodiment, a leaflet parting member 150 having internal threading 152 and positioned on the end of a shaft 154 couples to male threading 156 on the valve holder 142. The leaflet parting member 150 preferably fits snugly over the end of the shaft 154 with a slight interference, so that it may be decoupled therefrom with ease.

Attachment of the parting member 150 to the holder 142 is much as described above, wherein a technician passes the parting member 150 on the end of the shaft 154 through the coupling stent 160, parts the flexible leaflets 162 of the valve 140 from the inflow side, and screws the parting member to the male threading 156 of the holder 142. Once the technician firmly attaches the parting member 150, the entire valve/holder assembly may be easily pulled and removed from within the jar 26. At this stage, or after attachment of a valve delivery tube 170, the packaging sleeve 24 is removed, such as was shown for the first embodiment in FIGS. 10A-10C.

With or without the packaging sleeve 24, the valve delivery tube 170 inserts axially into a proximal end of the holder 142, and the shaft 154 originally attached to the leaflet parting member 150 is removed, resulting in the assembly shown in FIG. 14B. This configuration is substantially similar to that shown in FIG. 13 for the earlier embodiment, and the valve delivery procedure remains the same from that point on.

FIGS. 15A-15C and 16 depict an alternative packaged prosthetic heart valve assembly 180 that, as before, includes a jar 182 having a closed bottom 184 and a lid (not shown). The jar 182 receives a sub-assembly of a prosthetic heart valve 190 having an inflow end and an outflow end attached to a valve holder 192. The valve holder 192 mounts to a packaging sleeve 194 such that the heart valve 190 projects upward in the jar 182, and the holder downward. Since the holder 192 attaches to the outflow end of the valve, the inflow end of the valve projects upward toward the jar opening.

Figure 15C:
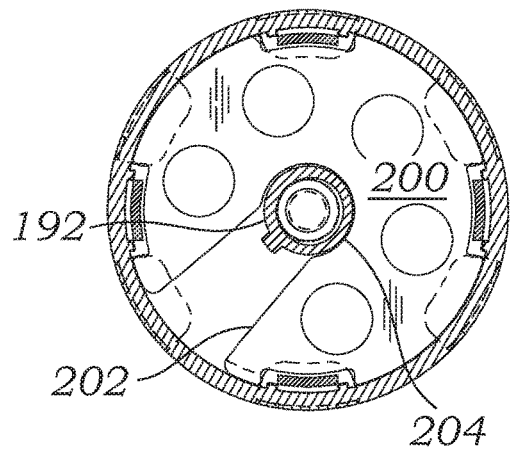
FIGS. 15A-15C are various elevation, and sectional views of an alternative packaged prosthetic heart valve assembly.

The packaging sleeve 194 defines a generally circular periphery as seen from above in FIG. 15C that fits closely within the jar 182, and has an axial dimension that extends substantially the entire axial height of the jar between the bottom 184 and the lid. The inner walls of the jar 182 and lid constrain the packaging sleeve 194 from substantial movement within the jar, and therefore the holder 192 and attached valve 190 are also stabilized from substantial movement.

Figure 16:
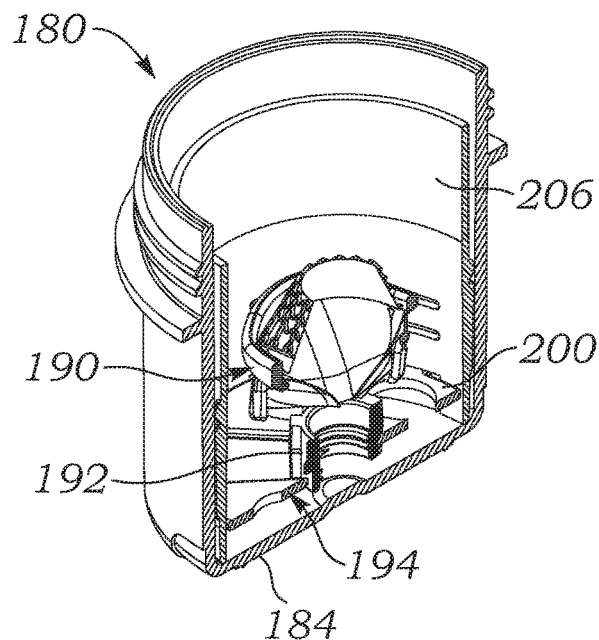
FIG. 16 is a detail sectional view of the valve and valve holder.
Figure 15A:
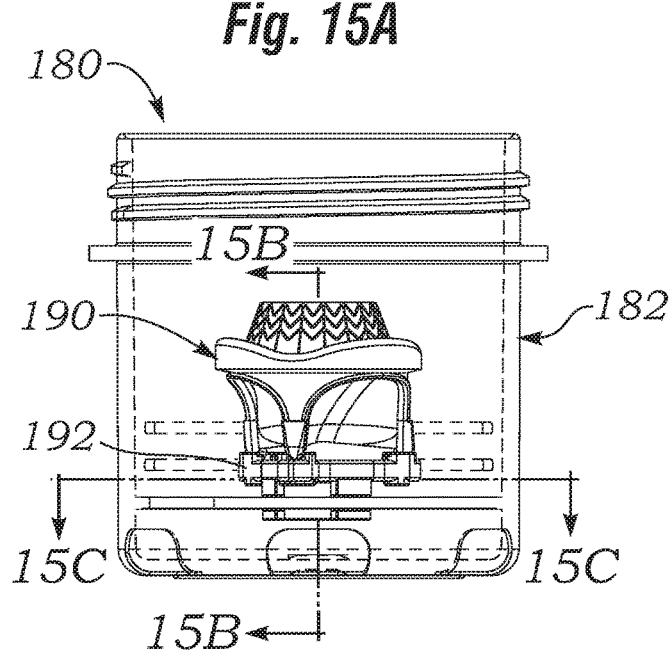
Figure 15B:
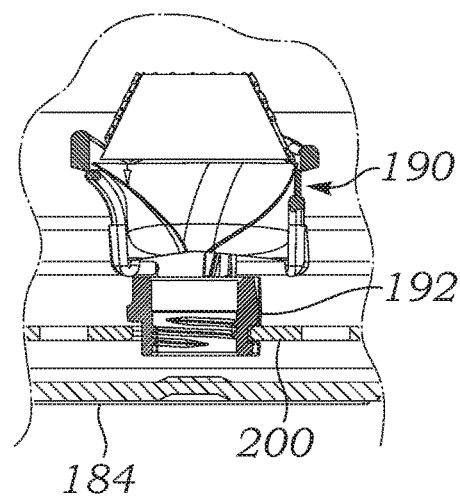

In illustrated embodiment, the packaging sleeve 194 features two components rather than one, as described above. A generally planar clip 200 extends radially across the interior of the jar 182 substantially closer to the jar bottom 184 than to the lid. As seen best in FIG. 15C, the clip 200 has an entry slot 202 extending from a peripheral edge to a central docking aperture 204 wider than the entry slot. The valve holder 192 includes a slot that couples to the docking aperture 204 such that the holder 192 is oriented toward the bottom 184 of the jar 182. The second component 206 circumscribes the clip 200 and extends substantially the entire axial height of the jar 182 between the bottom 184 and the lid. The second component 206 may take a variety of forms, and as illustrated has a tubular wall structure with a plurality of horizontal slots therein. At least two of the horizontal slots receive outwardly directed lugs on the peripheral edge of the planar clip 200, as seen in FIG. 16. When removed from the constraint of the jar 182, the tubular wall structure 206 may be detached from around the clip 200 for removal of the valve/holder sub-assembly. Preferably, however, a large circumferential break is provided in the tubular wall structure 206 aligned with and adjacent to the entry slot 202 so that the valve/holder sub-assembly may be detached from the clip 200 without separating the two components of the packaging sleeve 194.

The one- or two-piece packaging sleeves 24, 194 described above combine a clip to secure a valve holder and a sleeve that stabilizes the valve within the jar. The sleeves are been designed and developed for containment, stabilization, locking, protection and preservation of bioprosthetic valves, though certain features may be useful for other types of valves, in particular other flexible leaflet valves.

Desirably, the packaging sleeves 24, 194 are injection molded polypropylene and are intended to fit within storage jars having a volume of about 3.8 oz. Alternatively, the packaging sleeves 24, 194 can be produced from alternate manufacturing processes such as machining, pressure-forming, extrusion, vacuum forming, thermoforming, casting, blow molding, rotational molding, rim molding, rapid prototyping, etc.

The packaging sleeves 24, 194 provide at least the following advantages:
Contain the valve within the posts
Stabilize the valve during attachment of handle by preventing rotation
Lock the valve in position by the living hinge feature
Facilitate ease of access and attachment of delivery system
Promote ease of extraction of the valve from the jar
Allow for better aseptic handling of the product
Allow for easy detachment from the valve holder
Protect from distribution hazards
Allow for sterilization in solution While the invention has been described in its preferred embodiments, it is to be understood that the words which have been used are words of description and not of limitation. Therefore, changes may be made within the appended claims without departing from the true scope of the invention.

What is claimed is:

1. A method of preparing a packaged prosthetic heart valve for implant, comprising:
providing a packaged prosthetic heart valve having an inflow end and an outflow end, a valve holder that holds the valve during delivery attached to the outflow end of the valve and an assembly of the attached valve and holder being positioned within a jar having a closed bottom and an open top end closeable with a lid, the jar having an axial depth greater than the lid, with the holder located below the prosthetic heart valve when the assembly is stored within the jar;
extending a shaft through the middle of the heart valve from the inflow end to the outflow end and coupling the shaft to the valve holder; and
removing the assembly of the valve and holder from the jar using the shaft.

2. The method of claim 1, wherein the prosthetic heart valve comprises a plurality of flexible leaflets mounted to commissure posts around a peripheral non-expandable support structure with free edges that project toward an outflow direction and meet or coapt along a valve axis.

3. The method of claim 2, further comprising providing a leaflet parting member detachably mounted on the shaft that pushes past the flexible leaflets and couples to the valve holder.

4. The method of claim 3, wherein the leaflet parting member is removably attached to a distal end of the shaft such that the leaflet parting member directly couples to the valve holder.

5. The method of claim 4, wherein the leaflet parting member comprises threads that engage mating threads on the valve holder, the method comprising providing structure in the jar that prevents rotation of the valve holder relative to the jar in at least one direction.

6. The method of claim 4, wherein the leaflet parting member comprises a female receptacle with a series of axial grooves that receive axial ribs on the shaft which fit snugly into the axial grooves in an interference fit and transfer torque between the two elements.

7. The method of claim 4, wherein the method further includes attaching a valve delivery tube to the leaflet parting member from the outflow side of the valve, and detaching the shaft from the leaflet parting member.

8. The method of claim 7, wherein the leaflet parting member comprises an externally-threaded narrower distal portion that passes through and projects through the valve holder, and the valve delivery tube include female threads that mate with the leaflet parting member distal portion.

9. The method of claim 7, wherein the valve delivery tube provides an elongated access channel aligned with a bore through the valve holder, and the valve delivery tube include a proximal coupler on an end opposite the holder for attaching to additional components of a delivery system.

10. The method of claim 1, wherein the valve holder is attached to the prosthetic heart valve with at least one suture that passes through fabric in the valve and across a cutting guide in the holder to enable the holder to be pulled free from the valve when the suture is severed.

11. The method of claim 1, wherein the packaged prosthetic heart valve further comprises a packaging sleeve sized to fit closely within the jar and rest on the bottom thereof, the sleeve having structure to which the valve holder removably couples, the method comprising removing the assembly of the valve, holder and packaging sleeve from the jar using the shaft.

12. The method of claim 1, further including:
securing a valve delivery tube with respect to the valve holder on the outflow side of the valve; and
detaching the shaft from the valve holder.

13. A method of preparing a packaged prosthetic heart valve for implant, comprising:
opening a jar containing a packaged prosthetic heart valve having flexible leaflets therein, the heart valve having an inflow end and an outflow end, a valve holder that holds the valve during delivery attached to the outflow end of the valve and an assembly of the attached valve and holder being positioned in the jar with the holder oriented toward a closed bottom of the jar and the valve oriented toward an open top;
extending a shaft through the open top of the jar and through a middle of the heart valve from the inflow end to the outflow end past the flexible leaflets and coupling the shaft to the valve holder from an inflow side thereof;
removing the assembly of the valve and valve holder from the jar using the shaft; and
delivering the prosthetic heart valve to a target annulus, securing the prosthetic heart valve to the annulus, and detaching the valve holder from the prosthetic heart valve.

14. The method of claim 13, further including:
securing a valve delivery tube with respect to the valve holder on the outflow side of the valve; and
detaching the shaft from the valve holder.

15. The method of claim 13, wherein the flexible leaflets mount to commissure posts around a peripheral non-expandable support structure, with free edges of the flexible leaflets projecting toward an outflow direction and meeting or coapting along a valve axis.

16. The method of claim 13, further comprising providing a leaflet parting member detachably mounted on the shaft that pushes past the flexible leaflets and couples to the valve holder.

17. The method of claim 16, wherein the leaflet parting member is removably attached to a distal end of the shaft such that the leaflet parting member directly couples to the valve holder.

18. The method of claim 17, wherein the leaflet parting member comprises threads that engage mating threads on the valve holder, the method comprising providing structure in the jar that prevents rotation of the valve holder relative to the jar in at least one direction.

19. The method of claim 17, wherein the leaflet parting member comprises a female receptacle with a series of axial grooves that receive axial ribs on the shaft which fit snugly into the axial grooves in an interference fit and transfer torque between the two elements.

20. The method of claim 17, wherein the method further includes attaching a valve delivery tube to the leaflet parting member from the outflow side of the valve, and detaching the shaft from the leaflet parting member.

21. The method of claim 20, wherein the leaflet parting member comprises an externally-threaded narrower distal portion that passes through and projects through the valve holder, and the valve delivery tube include female threads that mate with the leaflet parting member distal portion.

22. The method of claim 20, wherein the valve delivery tube provides an elongated access channel aligned with a bore through the valve holder, and the valve delivery tube include a proximal coupler on an end opposite the holder for attaching to additional components of a delivery system.

23. The method of claim 13, wherein the valve holder is attached to the prosthetic heart valve with at least one suture that passes through fabric in the valve and across a cutting guide in the holder to enable the holder to be pulled free from the valve when the suture is severed.

24. The method of claim 13, wherein the packaged prosthetic heart valve further comprises a packaging sleeve sized to fit closely within the jar and rest on the bottom thereof, the sleeve having structure to which the valve holder removably couples, the method comprising removing the assembly of the valve, holder and packaging sleeve from the jar using the shaft.

* * * * *